(12) United States Patent
Lee et al.

(10) Patent No.: US 11,918,632 B2
(45) Date of Patent: Mar. 5, 2024

(54) PHARMACEUTICAL COMPOSITION FOR DIAGNOSING, PREVENTING OR TREATING LIVER CANCER USING SSU72 PROTEIN OR A POLYNUCLEOTIDE ENCODING THE SAME

(71) Applicants: CUROGEN TECHNOLOGY CO., LTD., Suwon-si (KR); RESEARCH & BUSINESS FOUNDATION SUNGKYUNKWAN UNIVERSITY, Suwon-si (KR)

(72) Inventors: Chang Woo Lee, Pohang-si (KR); Jin Kwan Lee, Suwon-si (KR); Hyun Soo Kim, Seoul (KR); Jae-kyung Kim, Suwon-si (KR); Joon Sup Yoon, Seoul (KR)

(73) Assignees: CUROGEN TECHNOLOGY CO., LTD., Suwon-si (KR); RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 0 days.

(21) Appl. No.: 17/814,579

(22) Filed: Jul. 25, 2022

(65) Prior Publication Data
US 2022/0401526 A1 Dec. 22, 2022

Related U.S. Application Data

(63) Continuation-in-part of application No. PCT/IB2022/050421, filed on Jan. 19, 2022.

(30) Foreign Application Priority Data

Jan. 20, 2021 (KR) .................. 10-2021-0008251

(51) Int. Cl.
| | | |
|---|---|---|
| A61P 1/16 | (2006.01) |
| A61K 38/46 | (2006.01) |
| A61K 48/00 | (2006.01) |
| A61P 35/00 | (2006.01) |
| C12N 15/86 | (2006.01) |
| C12N 15/861 | (2006.01) |
| G01N 33/574 | (2006.01) |
| G01N 33/68 | (2006.01) |

(52) U.S. Cl.
CPC .............. *A61K 38/465* (2013.01); *A61P 1/16* (2018.01); *A61P 35/00* (2018.01); *C12N 15/86* (2013.01); *C12Y 301/03016* (2013.01); *G01N 33/57438* (2013.01); *G01N 33/57484* (2013.01); *G01N 33/6893* (2013.01); *A61K 48/00* (2013.01); *C12N 2750/14143* (2013.01); *C12N 2750/14171* (2013.01)

(58) Field of Classification Search
CPC .. A61K 38/1709; A61K 38/465; A61K 38/48; C12N 15/86
See application file for complete search history.

(56) References Cited

U.S. PATENT DOCUMENTS

2018/0140681 A1 5/2018 Cho et al.

FOREIGN PATENT DOCUMENTS

| KR | 1020160054719 | * 10/2014 | ............. G01N 33/15 |
| KR | 20160054719 | 5/2016 | |

OTHER PUBLICATIONS

Kattenhorn et al. Adeno-associated virus gene therapy for liver diseases. Human Gene Therapy. 27(12): 947-961. (Year: 2016).*
Sang Hoon Ahn et al., "Long-term clinical and histological outcomes in patients with spontaneous hepatitis B surface antigen seroclearance", Journal of Hepatology, vol. 42, Issue 2, Feb. 2005, pp. 188-194.
Giuseppe Montalto et al., "Epidemiology, Risk Factors, and Natural History of Hepatocellular Carcinoma", Ann. N.Y. Acad. Sci. 963: 13-20 (2002).
Jeong-Ju Yoo et al., "Recent research trends and updates on non-alcoholic fatty liver disease", Clinical and Molecular Hepatology 2019;25:1-11, https://doi.org/10.3350/cmh.2018.0037.

* cited by examiner

*Primary Examiner* — Marsha Tsay
(74) *Attorney, Agent, or Firm* — LEX IP MEISTER, PLLC

(57) ABSTRACT

The present invention provides a method for preventing or treating liver cancer in a subject comprising administrating at least one selected from the group consisting of an Ssu72 peptide, a polynucleotide encoding the Ssu72 peptide and an expression vector containing the polynucleotide to the subject.

6 Claims, 17 Drawing Sheets
Specification includes a Sequence Listing.

Scale bar = 100 μm

H & E staining

SEQUENCE LISTING

```
Sequence total quantity: 3
SEQ ID NO: 1            moltype = AA  length = 194
FEATURE                 Location/Qualifiers
source                  1..194
                        mol_type = protein
                        organism = Homo sapiens
SEQUENCE: 1
MPSSPLRVAV VCSSNQNRSM EAHNILSKRG FSVRSFGTGT HVKLPGPAPD KPNVYDFKTT  60
YDQMYNDLLR KDKELYTQNG ILHMLDRNKR IKPRPERFQN CKDLFDLILT CEERVYDQVV 120
EDLNSREQET CQPVHVVNVD IQDNHEEATL GAFLICELCQ CIQHTEDMEN EIDELLQEFE 180
EKSGRTFLHT VCFY                                                  194

SEQ ID NO: 2            moltype = DNA  length = 585
FEATURE                 Location/Qualifiers
source                  1..585
                        mol_type = genomic DNA
                        organism = Homo sapiens
SEQUENCE: 2
atgccgtcgt ccccgctgcg ggtggcggtg gtgtgctcga gcaaccagaa ccggagcatg  60
gaggcgcaca acatcctcag caaacgggga ttcagcgtcc gatcctttgg aacagggact 120
cacgtgaagc ttccaggacc agctcccgac aagcccaatg tttatgattt caaaaccaca 180
tatgaccaga tgtacaatga tcttcttagg aaagacaaag aactctatac acagaatggg 240
attttacata tgctggacag aaataagaga atcaagcccc ggccagaaag attccagaac 300
tgcaaagacc tgtttgatct gatcctcact tgcgaagaga gagtgtatga ccaggtggtg 360
gaagatctga attccagaga acaggagacc tgccagcctg tgcacgtggt caatgtggac 420
atccaggaca accacgagga ggccaccctg ggggcgtttc tcatctgtga gctctgccag 480
tgtatccagc acacggaaga catggagaac gagatcgacg agctgctgca ggagttcgag 540
gagaagagtg gccgcacctt tctgcacacc gtctgcttct actga              585

SEQ ID NO: 3            moltype = DNA  length = 410
FEATURE                 Location/Qualifiers
misc_feature            1..410
                        note = TBG promoter
source                  1..410
                        mol_type = other DNA
                        organism = Homo sapiens
SEQUENCE: 3
tgcatgtata atttctacag aacctattag aaaggatcac ccagcctctg cttttgtaca  60
actttccctc aaaaaactgc caattccact gctgtttggc ccaatagtga gaactttttc 120
ctgctgcctc ttggtgcttt tgcctatggc ccctattctg cctgctgaag acactcttgc 180
cagcatggac ttaaacccct ccagctctga caatcctctt tctcttttgt tttacatgaa 240
gggtctggca gccaaagcaa tcactcaaag ttcaaacctt atcatttttt gctttgttcc 300
tcttggcctt ggttttgtac atcagctttg aaaataccat cccagggtta atgctggggt 360
taatttataa ctaagagtgc tctagttttg caatacagga catgctataa              410
```

PHARMACEUTICAL COMPOSITION FOR DIAGNOSING, PREVENTING OR TREATING LIVER CANCER USING SSU72 PROTEIN OR A POLYNUCLEOTIDE ENCODING THE SAME

CROSS REFERENCE TO RELATED APPLICATIONS

This application claims priority to Korean Patent Application No. 2021-0008251 filed on Jan. 20, 2021. In addition, this application is a continuation-in-part of an International Patent Application No. PCT/IB2022/050421 filed on Jan. 19, 2022. Both of the above applications are incorporated herein by reference in their entirety.

REFERENCE TO AN ELECTRONIC SEQUENCE LISTING

The contents of the electronic sequence listing (SPJ20225254US sequence listing.xml; Size: 6 K bytes; and Date of Creation: Jul. 25, 2022) is herein incorporated by reference in its entirety. The contents of the electronic sequence listing in no way introduces new matter into the specification.

TECHNICAL FIELD

The present invention relates to a pharmaceutical composition or a method for treating liver cancer, and more particularly, the present invention relates to a pharmaceutical composition or a method for preventing, alleviating or treating liver cancer using an Ssu72 protein or a polynucleotide encoding the Ssu72 protein.

BACKGROUND ART

According to the Global Burden of Disease (GBD) 2019 report, liver cirrhosis ranks sixth in terms of year of life lost (YLL), and liver cancer ranks fifth in terms of the number of years of life lost due to premature death. Liver cirrhosis and liver cancer are mainly caused by slowly progressing chronic liver diseases such as chronic viral hepatitis or fatty liver disease, and this chronic liver diseases have no clear symptoms, and hepatic fibrosis gradually accumulates and irreversibly damages the liver, which is why it is called a 'silent killer'. The occurrence of metabolic syndrome has increased due to the lifestyle of modern society and westernized eating habits, and the liver, which is the most important metabolic organ of the body, is chronically severely affected. Liver disease, particularly, non-alcoholic liver fatty disease (NALFD) is steadily increasing worldwide, and despite active health policies, it is difficult to reduce them due to reduced physical activities and aging population. The NAFLD has a high risk of metabolic syndrome regardless of obesity, and insulin resistance, inflammatory cytokine secretion, dyslipidemia, and fibrinolytic factor are involved as pathological mechanisms. It can progress to serious liver diseases such as non-alcoholic steatohepatitis (NASH), hepatocellular carcinoma (HCC), and liver fibrosis. Recently, studies to alleviate inflammation and fibrosis in the liver are continuing and various drugs are being developed, but no drug officially approved by the FDA so far (Yoo, J. J. et al., *Clin. Mol. Hepatol.* 25: 1-11, 2019). Liver cancer is also being treated with surgical treatments such as liver transplantation and liver resection, and non-surgical treatments such as local therapy, transcatheter arterial chemoembolization (TACE), radiation therapy, immunotherapy, and systemic chemotherapy, but it is a chronic disease accompanying cancer. With cirrhosis and chronic hepatitis, the cancer treatment effect is insufficient.

SUMMARY OF THE INVENTION

However, in the case of the prior arts, there is a problem in that the treatment efficiency is not high along with side effects such as chronic hepatitis and liver cirrhosis.

The present invention is devised to solve various problems, including the above problems, the object of the present invention is to provide a pharmaceutical composition for preventing or treating liver cancer with high sensitivity and specificity, without side effects. However, these problems are exemplary, and the scope of the present invention is not limited thereto.

In an aspect of the present invention, there is provided a method for treating a patient suffering from liver cancer comprising administrating to the patient at least one selected from the group consisting of:

a Ssu72 peptide, a polynucleotide encoding the Ssu72 peptide, and an expression vector comprising the polynucleotide.

In another aspect of the present invention, there is provided a method of determining type of a liver cancer in a patient comprising:

measuring the expression level of Ssu72 or activity of the Ssu72 in a cancer tissue obtained from the patient; and determining that the liver cancer is NASH-derived hepatocellular carcinoma when the expression level of Ssu72 in the cancer tissue is lower than that of a normal subject or a normal liver tissue of the patient or the Ssu72 is expressed as an inactive form in the cancer tissue.

In another aspect of the present invention, there is provided a method of predicting the likelihood of occurrence of liver cancer in a subject comprising:

measuring the expression level of Ssu72 or activity of the Ssu72 in a sample obtained from the subject; and determining that the subject is likely to develop nonalcoholic liver fatty disease (NASH)-derived hepatocellular carcinoma (HCC) when the expression level of Ssu72 is lower than that of a normal subject or normal tissues of the subject or the Ssu72 is expressed as an inactive form.

In another aspect of the present invention, there is provided a method of preventing liver cancer in a subject comprising:

administering Ssu72 peptide consisting of the amino acid sequence represented by SEQ ID NO: 1, a polynucleotide encoding the Ssu72 peptide, or an expression vector comprising the polynucleotide to the subject.

In another aspect of the present invention, there is provided a method of determining type of a liver cancer in a patient comprising:

measuring the expression level of Ssu72 or activity of the Ssu72 in a cancer tissue obtained from the patient; and determining that the liver cancer is NASH-derived hepatocellular carcinoma when the expression level of Ssu72 in the cancer tissue is lower than that of a normal subject or a normal liver tissue of the patient or the Ssu72 is expressed as an inactive form in the cancer tissue.

In another aspect of the present invention, there is provided a method of screening drug candidate for treating liver cancer comprising:

treating a candidate substance in the hepatocytes in culture or experimental animals except humans;

measuring the expression of Ssu72 or the interaction between the Ssu72 and HNF4a in the hepatocyte or the experimental animals; and selecting a candidate substance that increases the expression of Ssu72 or the interaction between Ssu72 and HNF4a in the hepatocytes or experimental animals.

In another aspect of the present invention, there is provided a pharmaceutical composition for treating liver cancer comprising Ssu72 peptide consisting of the amino acid sequence represented by SEQ ID NO: 1, a polynucleotide encoding the Ssu72 peptide, or an expression vector comprising the polynucleotide as an active ingredient.

In another aspect of the present invention, there is provided a pharmaceutical composition for preventing liver cancer comprising Ssu72 peptide consisting of the amino acid sequence represented by SEQ ID NO: 1, a polynucleotide encoding the Ssu72 peptide, or an expression vector comprising the polynucleotide as an active ingredient.

In another aspect of the present invention, there is provided a pharmaceutical composition for treating liver cancer comprising Ssu72 peptide consisting of the amino acid sequence represented by SEQ ID NO: 1, a polynucleotide encoding the Ssu72 peptide, or an expression vector comprising the polynucleotide as an active ingredient.

In another aspect of the present invention, there is provided a pharmaceutical composition for preventing liver cancer comprising Ssu72 peptide consisting of the amino acid sequence represented by SEQ ID NO: 1, a polynucleotide encoding the Ssu72 peptide, or an expression vector comprising the polynucleotide as an active ingredient.

Advantageous Effects

The pharmaceutical composition according to an embodiment of the present invention can be used for the treatment of liver cancer, especially, hepatocellular carcinoma (HCC) derived from NAFLD (nonalcoholic fatty liver disease) since Ssu72, which is an active ingredient inhibits lipid deposition and liver fibrosis in the liver in a subject even though the subject is accustomed to a high-fat diet as well as exposed to chronic hepatotoxic chemicals. Furthermore, the pharmaceutical composition of the present invention has the potential to be used in the treatment of HCC caused by genetic causes.

BRIEF DESCRIPTIONS OF DRAWINGS

FIG. 1 is a schematic diagram illustrating the structure of pCMV.HA-Ssu72 vector as a non-viral vector according to an embodiment of the present invention used in the example of the present invention.

FIG. 2 is a schematic diagram representing procedure of preparing AAV8.TBG.HA-Ssu72 vector as a viral vector according to an embodiment of the present invention and strategies to package recombinant adeno-associated viruses (AAVs) expressing Ssu72 gene driven by the Thyroxine-binding globulin (TBG) promoter according to an embodiment of the present invention. TBG promoter described in FIG. 2 was used for liver-specific expression of Ssu72 in the AAV viral vector.

Figure 5A:
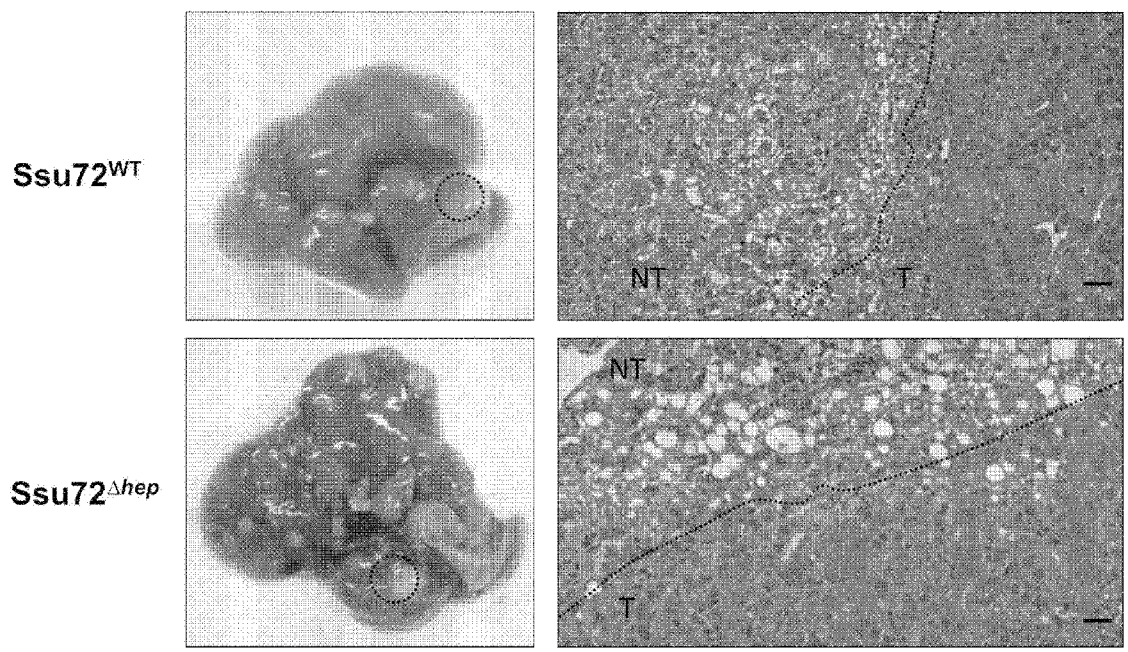

FIG. 5A shows a series of representative photographs of appearances (left) and internal structures (right) of livers excised from STAM model mice in which liver fibrosis and liver cancer were induced by injecting Streptozotocin 2 days after birth and feeding a high-fat diet 4 weeks after birth to the Ssu72$^{WT}$ (upper) and Ssu72$^{\Delta hep}$ (lower) mice, respectively. The representative photographs of internal structures of livers were taken by microscopic imaging after H&E staining.

Figure 5B:
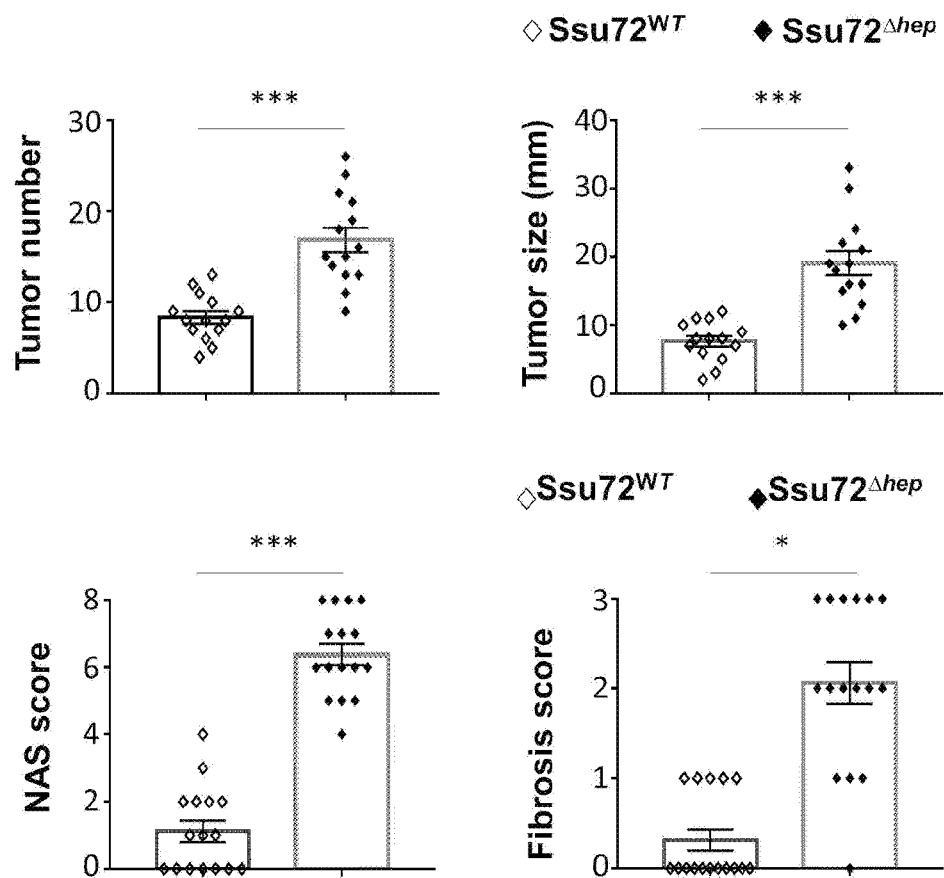

FIG. 5B is a series of graphs showing the results of analyzing the number of tumor nodules (upper left), tumor size (upper right), nonalcoholic fatty liver disease (NAFLD) activity score (NAS, lower left), and fibrosis score (lower right) in the excised livers from experimental animals 4 months after applying the STAM model to the Ssu72$^{WT}$ (◇) and Ssu72$^{\Delta hep}$ (◆) mice.

Figure 6A:
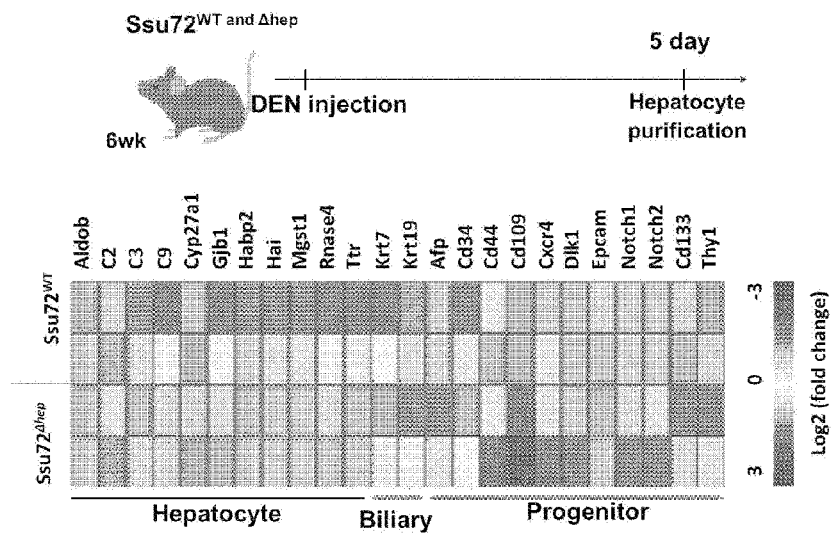

FIG. 6A is a heatmap graph representing downregulated or upregulated genes for hepatocyte-, biliary- and progenitor-marker between DEN-treated Ssu72$^{WT}$ and Ssu72$^{\Delta hep}$ mice using RNA-Seq for isolated hepatocytes in DEN-treated Ssu72$^{WT}$ and Ssu72$^{\Delta hep}$ mice. Particularly, 6-week-old Ssu72$^{WT}$ and Ssu72$^{\Delta hep}$ mice were treated with DEN (150 mg/kg) and the hepatocytes of the mice were isolated from the liver after 5 days (n=2 mice per group). The color bar represents the gradient of the log$_2$-fold change.

Figure 6B:
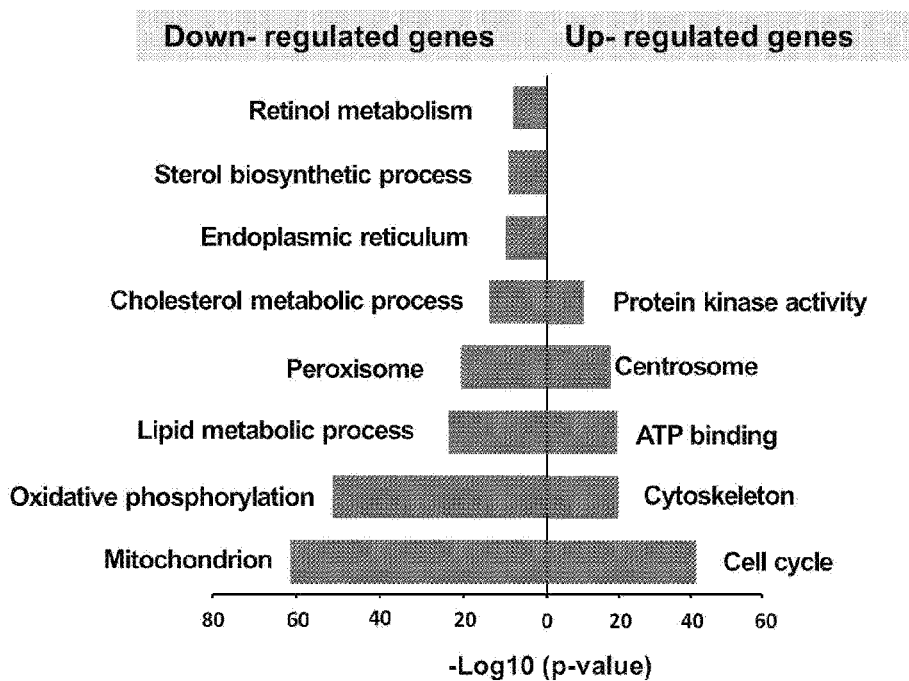

FIG. 6B shows a result of grouping genes according to functions thereof after classifying them downregulated and upregulated ones from the analysis of changes of gene expression obtained by RNA-Seq analysis for hepatocytes isolated from Ssu72$^{WT}$ and Ssu72$^{\Delta hep}$ mice treated with DEN, respectively. FIG. 6b is a graph listing genes with high significance through gene ontology analysis based on DAVID. The color bar represents the gradient of the log$_2$-fold change.

Figure 6C:
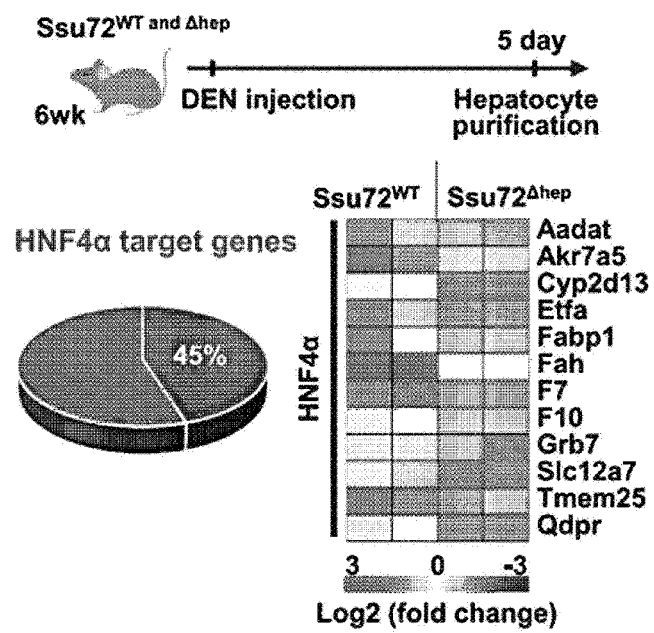

FIG. 6C is a heatmap graph representing HNF4α target genes among genes downregulated in hepatocytes from Ssu72$^{\Delta hep}$ mice compared to Ssu72$^{WT}$ mice using RNA-Seq on hepatocytes isolated from DEN-treated Ssu72$^{WT}$ and Ssu72$^{\Delta hep}$ mice. The pie chart indicates that 45% of all downregulated genes are HNF4α target genes.

Figure 6D:
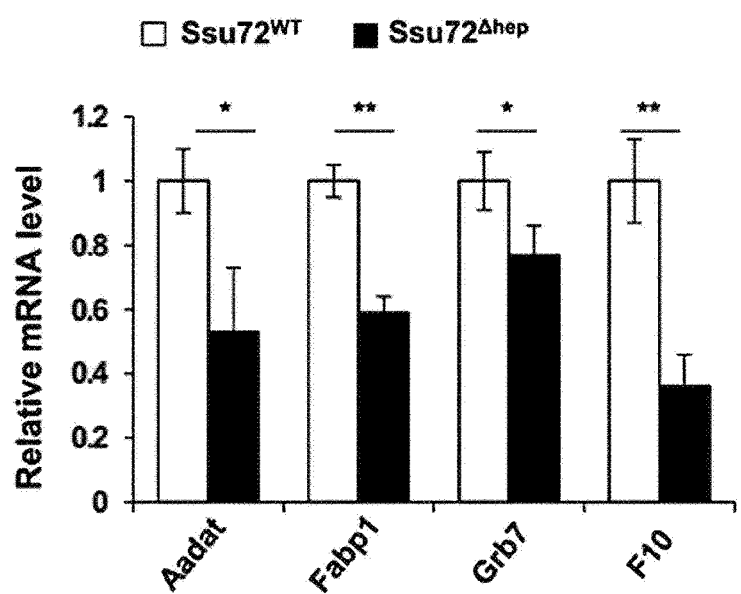

FIG. 6D is a graph showing the results of further analysis of four HNF4α target genes downregulated in hepatocytes derived from Ssu72$^{\Delta hep}$ compared to Ssu72$^{WT}$ mice using qRT-PCR from the results of gene analysis using RNA-Seq on hepatocytes isolated from DEN-treated Ssu72$^{WT}$ and Ssu72$^{\Delta hep}$ mice.

Figure 6E:
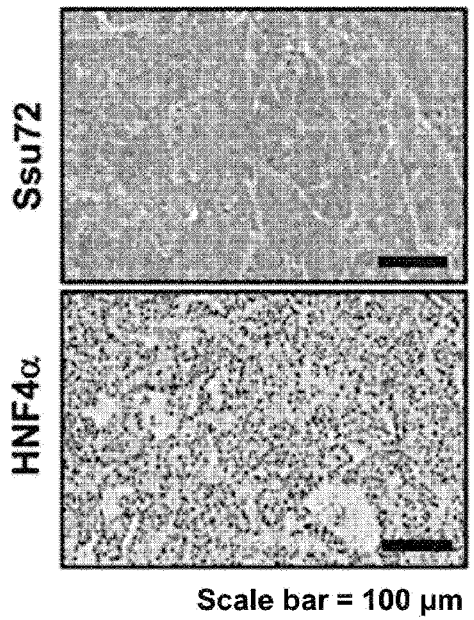
Figure 6E:
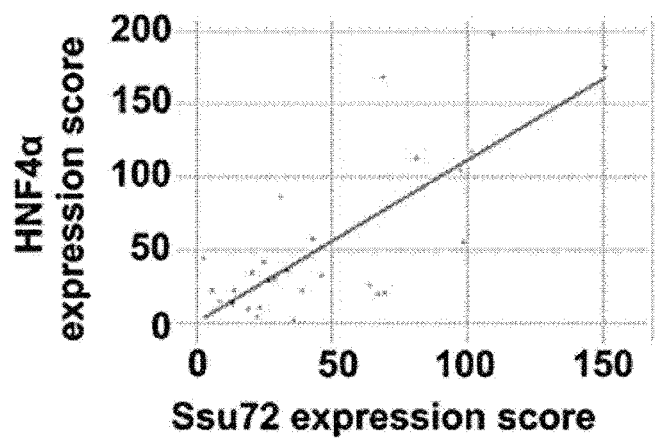

FIG. 6E shows a representative photograph representing results of immunohistochemical (IHC) staining with anti-Ssu72 antibodies and anti-HNF4α antibodies in 31 NASH-related HCC patients (upper) and a graph quantifying staining intensity of the IHC analysis (scale bar=100 µm, lower). The scatterplot shows a significant correlation between Ssu72 and HNF4α expression in the samples of NASH-related HCC patients (bottom, n=31).

Figure 6F:
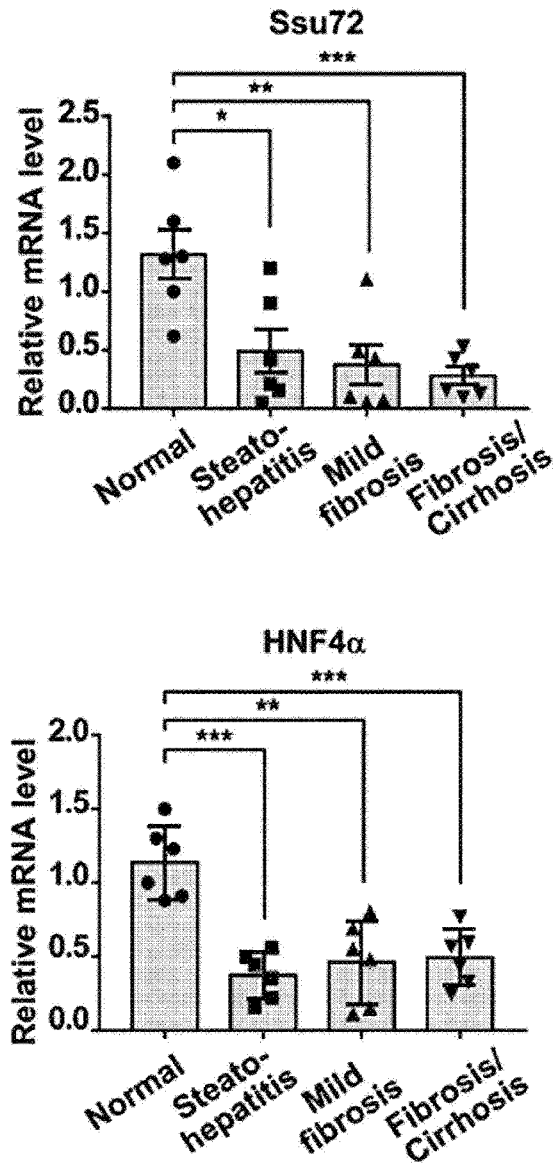

FIG. 6F is a series of graphs representing results of comparison and analysis of the relative expression levels of Ssu72 (upper) and HNF4α (lower) mRNA in samples from normal subjects (diagnosed as normalities, n=10), subjects suffering from mild fibrosis (n=70), and fibrosis/hepatic cirrhosis (n=105), respectively.

Figure 7A:
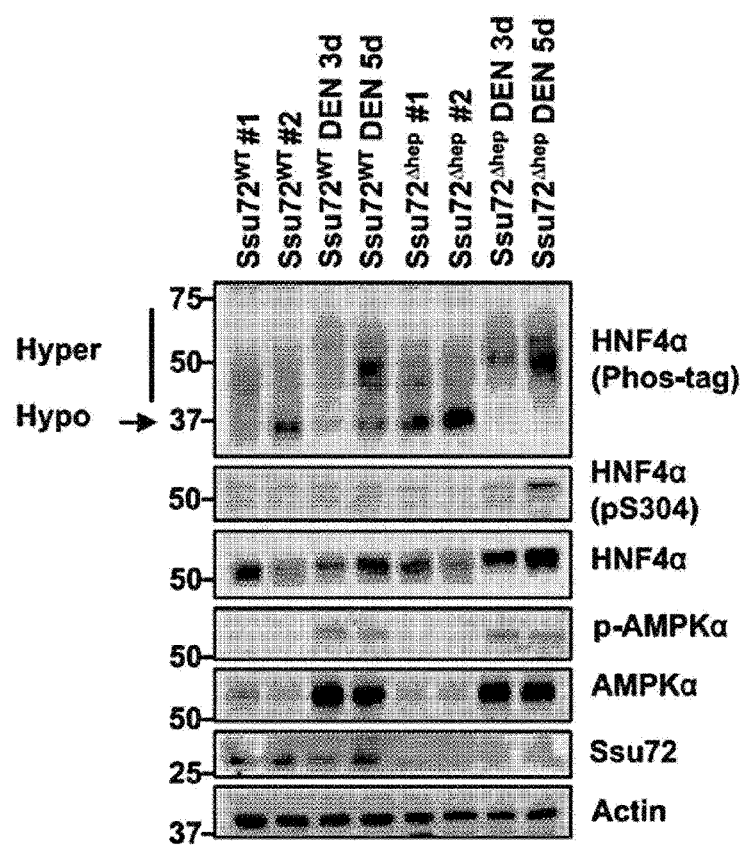

FIG. 7A is a photograph of immunoblot representing the results of immunoblotting of HNF4a, phosphorylated-HNF4α on serine 304 (pS304), AMPKα, phosphorylated-AMPKα, Ssu72 and Actin using liver extracts of $Ssu72^{WT}$ and $Ssu72^{\Delta hep}$ mice in order to confirm the relationship between HNF4α and Ssu72. DEN (150 mg/kg) was administered to 5-week-old $Ssu72^{WT}$ and $Ssu72^{\Delta hep}$ mice, and livers of the $Ssu72^{WT}$ and $Ssu72^{\Delta hep}$ mice was excised on 3 days and 5 days. Phos-tag represents the change in mobility of phosphorylated proteins using phospho-tag gel.

Figure 7B:
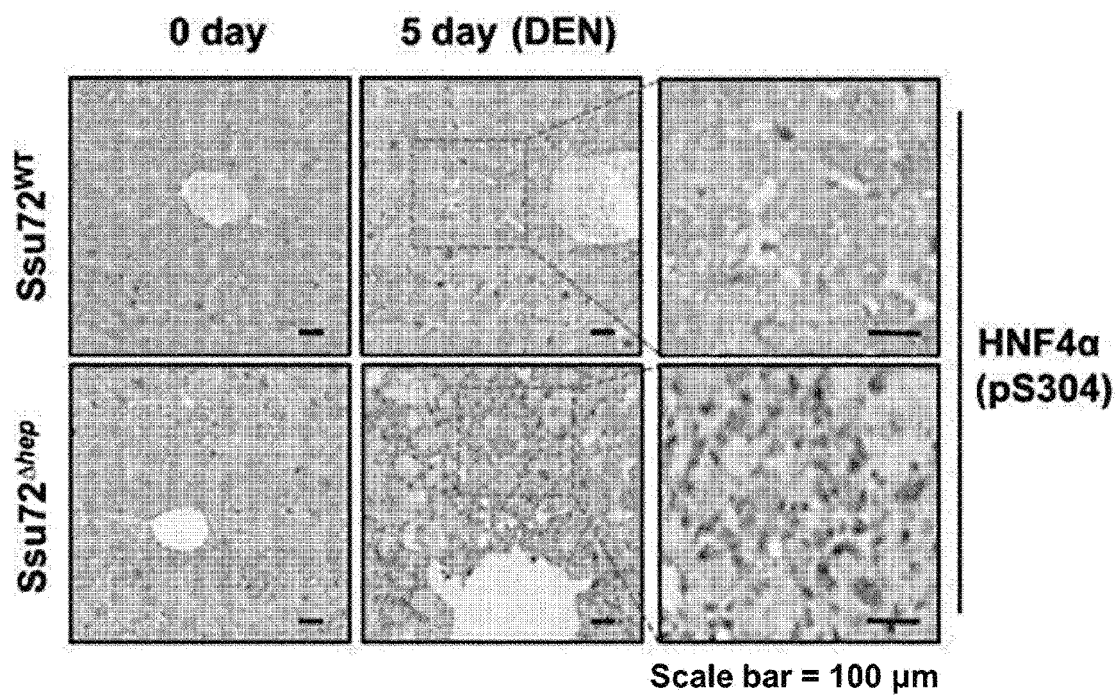

FIG. 7B is an IHC staining result of phospho-HNF4α (pS304) for livers of $Ssu72^{WT}$ and $Ssu72^{\Delta hep}$ mice treated with DEN in order to confirm the relationship between HNF4α and Ssu72.

Figure 7C:
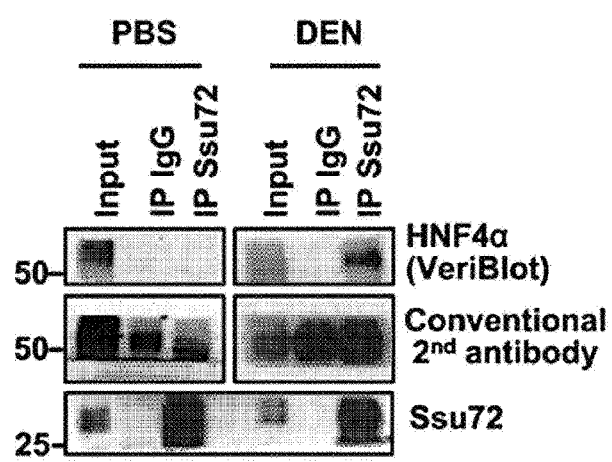

FIG. 7C is the results of immunoblot analysis using anti-HNF4α, anti-Ssu72 and conventional secondary antibodies in order to confirm the interaction between HNF4α and Ssu72. Liver extract from the PBS- or DEN-treated $Ssu72^{WT}$ mice were immunoprecipitated with anti-Ssu72 antibodies. Co-immunoprecipitated HNF4α was detected using VeriBlot secondary antibodies without masking by IgG heavy chains.

Figure 7D:
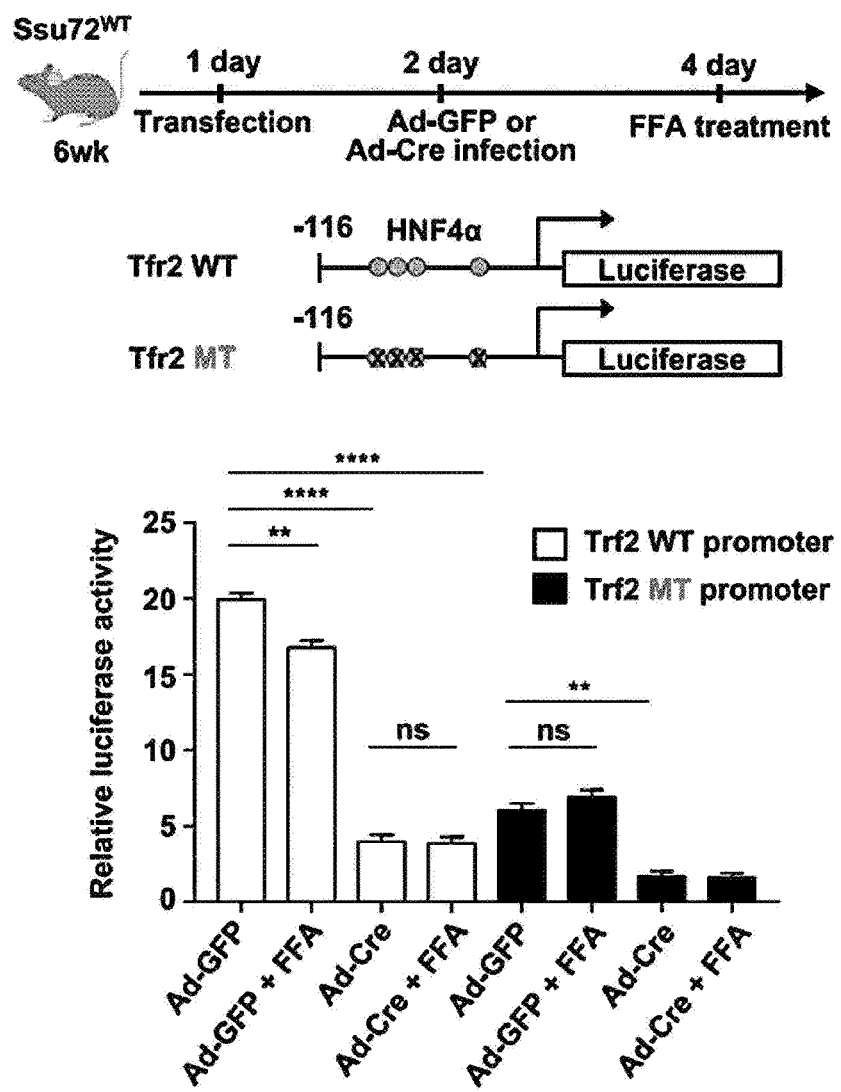

FIG. 7D shows a schematic diagram representing a schedule for an experiment performed in order to investigate the relationship between HNF4α transcriptional activity and Ssu72 expression under hepatocyte damage (upper); a gene map representing the structures of gene constructs for the experiment (middle); and a graph (bottom) representing the results of analysis of relative luciferase activity in the hepatocytes isolated from $Ssu72^{WT}$ mice after transfecting the hepatocytes with $Tfr2^{WT}$, $Tfr2^{MT}$, and control promoter plasmid, respectively and infecting the transfected hepatocytes with control (Ad-GFP) or Cre (Ad-Cre) adenovirus on day 1 from the transfection, and inducing hepatocyte damage by treating the hepatocytes with free fatty acid (FFA), such as palmitic acid, on day 3 from the transfection.

Figure 8A:
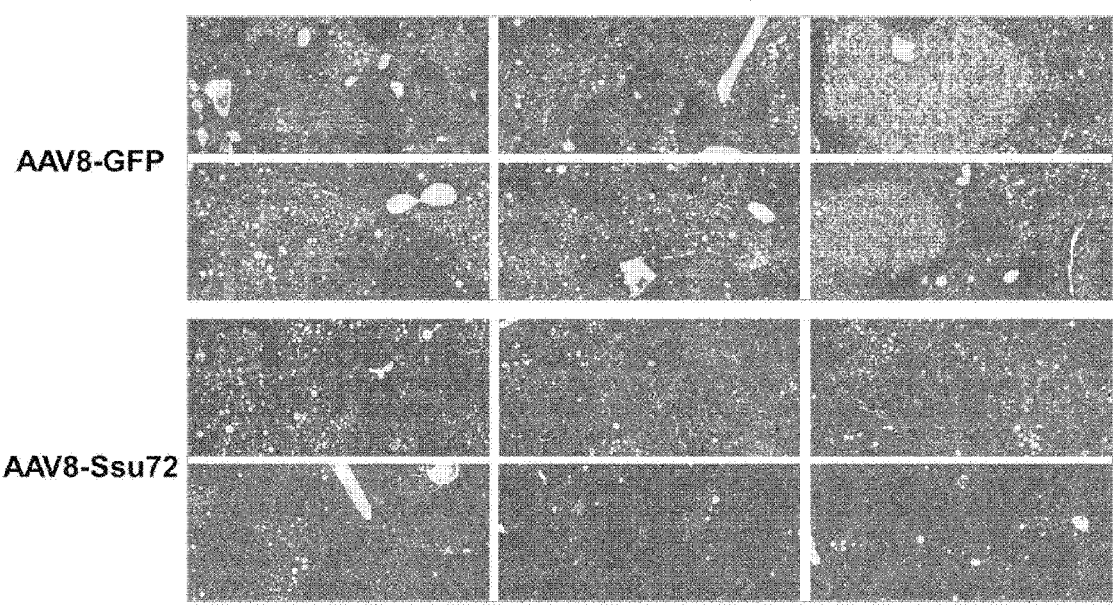

FIG. 8A is a microscopic image of liver tissues from NASH/HCC-induced mice by applying STAM model to normal mice which are stained with hematoxylin & Eosin (H&E) after injecting AAV8-Ssu72 as a therapeutic or AAV8-GFP as a control to the mice at 8 weeks of age. The mice were sacrificed, and their livers were excised at 4 weeks after the injection.

Figure 8B:
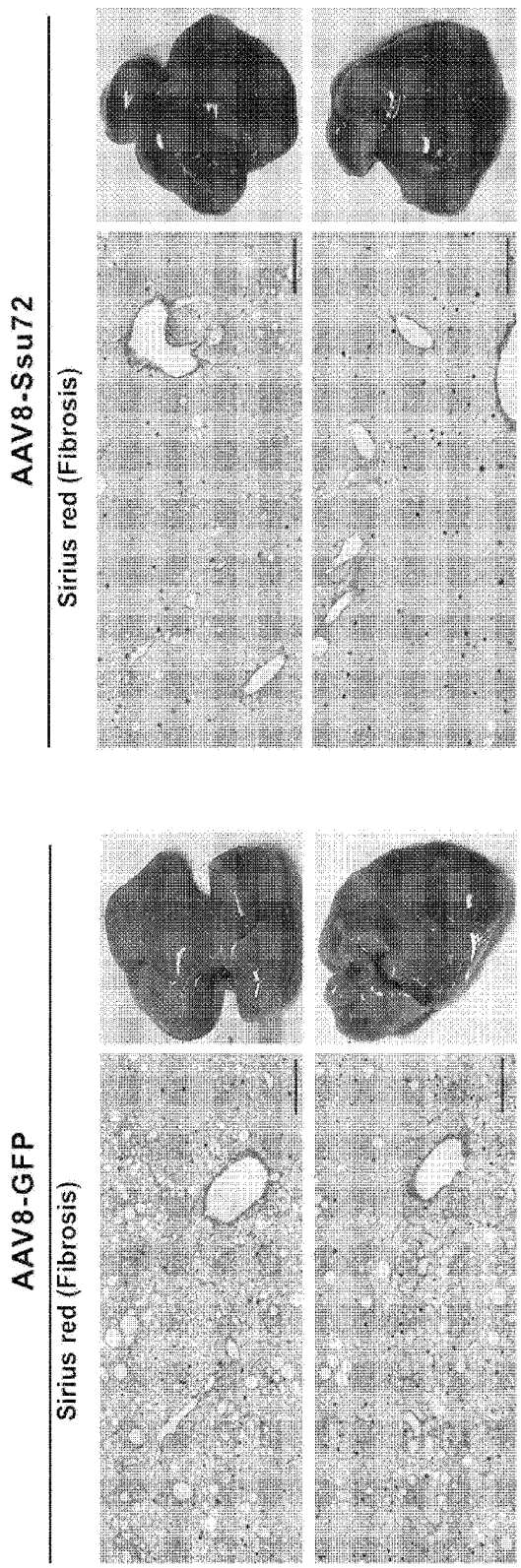

FIG. 8B is a series of photographs showing the results of measuring the degree of fibrosis by staining liver tissue sections obtained from the STAM model-applied mice sacrificed after 4 weeks from administering AAV8-GFP (left) or AAV8-Ssu72 (right) to the mice at 8 weeks of age with a Sirius red and whole appearance of excised livers.

Figure 8C:
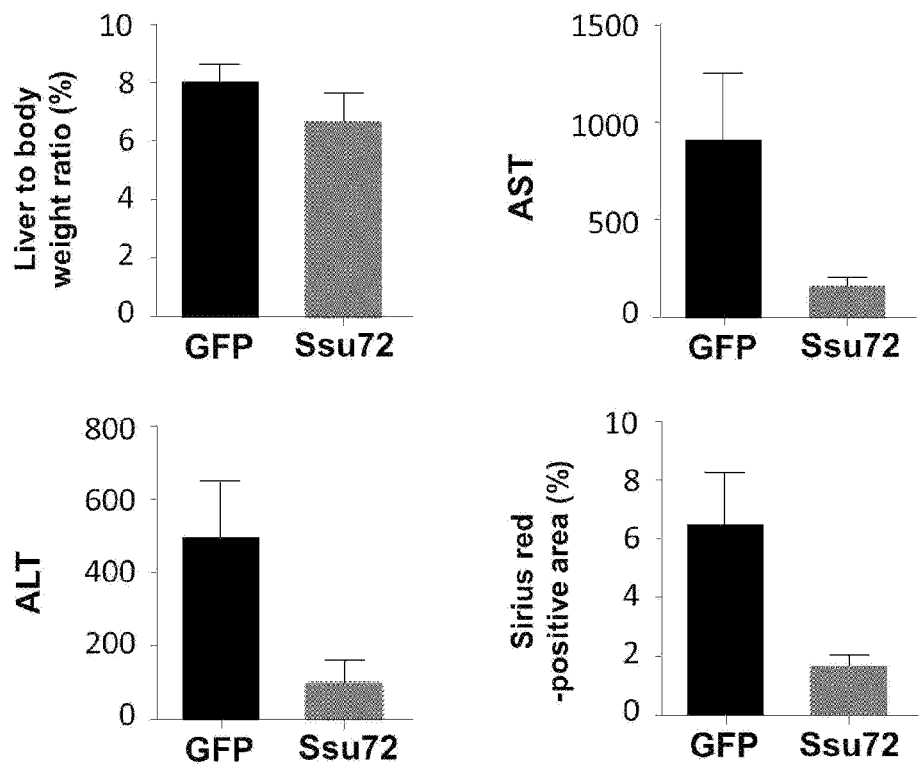

FIG. 8C is a series of graphs showing the results of analyzing body weight-to-weight of liver, level of AST and ALT obtained through serochemical analysis and area ratio of tissue stained with Sirius red in liver tissues excised from STAM model-applied mice.

Figure 9A:
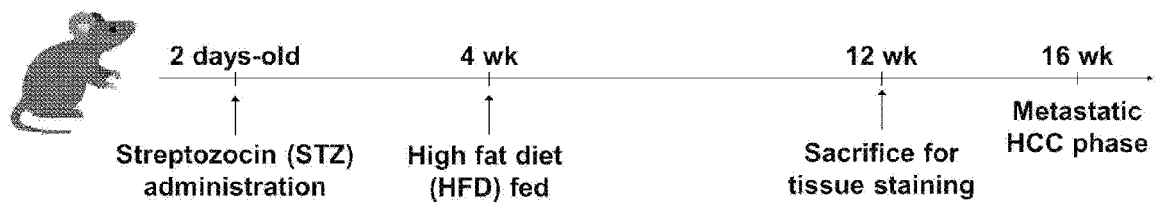

FIG. 9A is a schematic diagram representing an experimental schedule for analyzing the degree of the induction of liver cancer after applying a STAM model to wild-type mice.

Figure 9B:
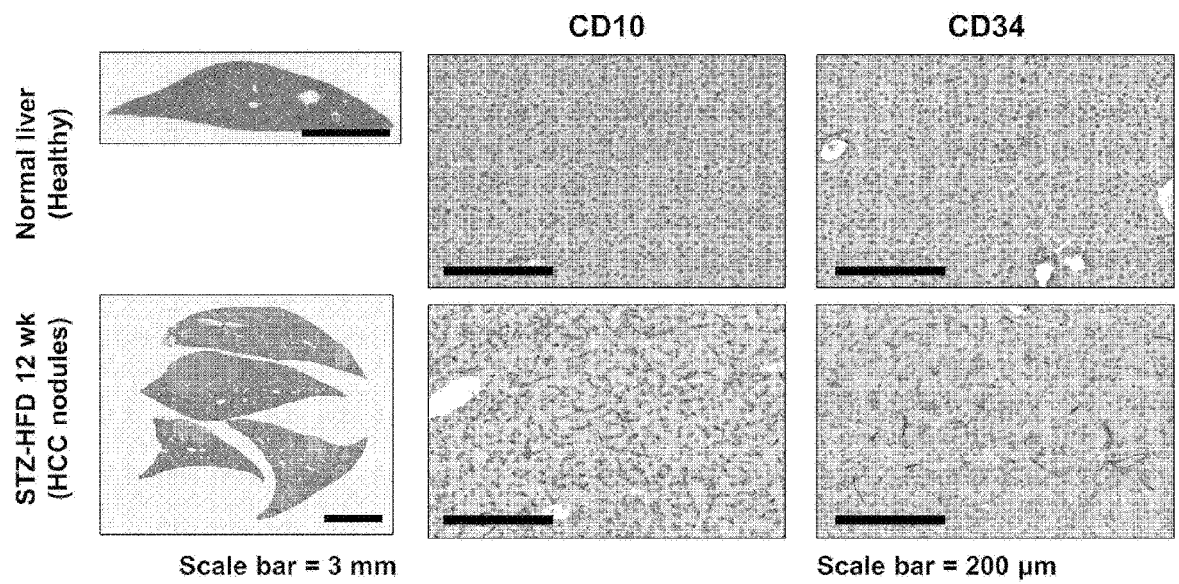
Figure 9B:
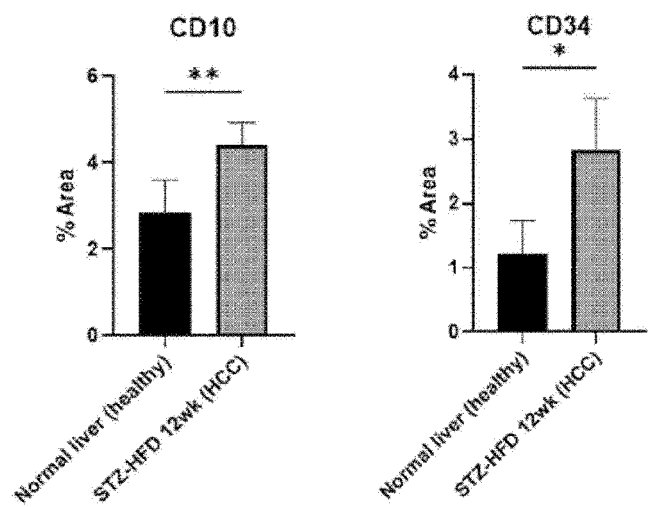

FIG. 9B shows a series of photographs representing of the results of H&E staining and immunohistochemistry (IHC) analysis for CD10 and CD34 which are standard markers for HCC in liver tissues sacrificed at 12 weeks after the application of the STAM model in wild-type mice (upper) and a series of graphs representing quantifying the results of the above IHC analysis (lower).

Figure 9C:
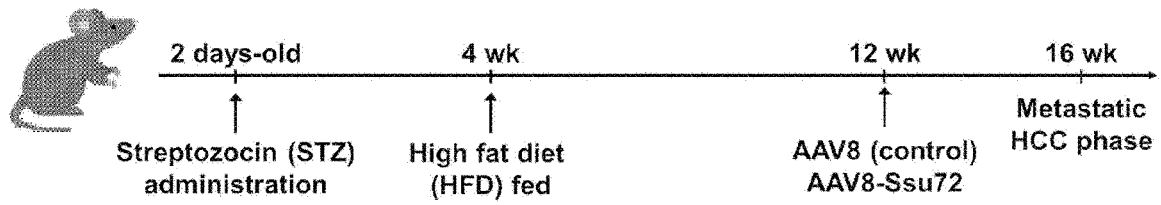

FIG. 9C is a schematic diagram representing an experimental schedule for investigating therapeutic effects of Ssu72 on HCC by injecting AAV8 or AAV8 Ssu72 at 12 weeks after applying the STAM model in wild-type mice and sacrificing them 4 weeks later.

Figure 9D:
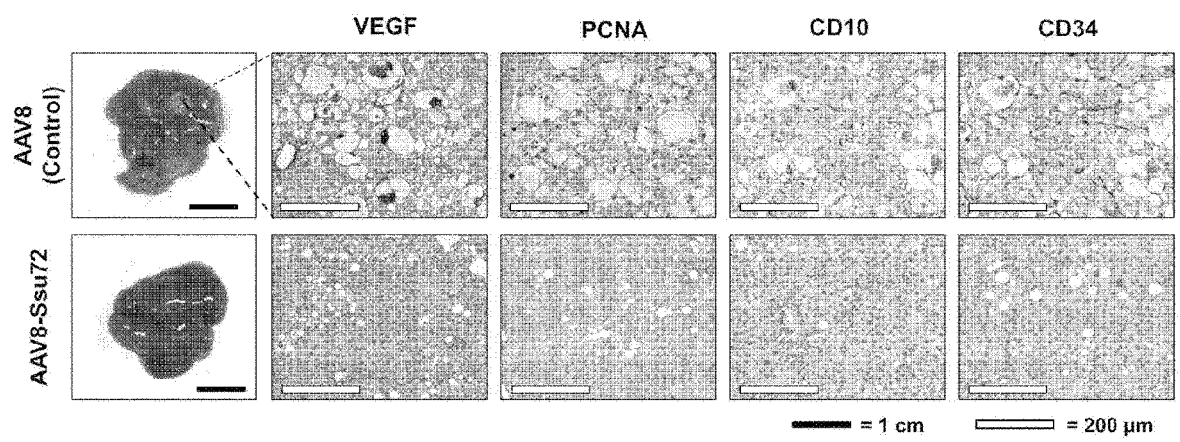
Figure 9D:
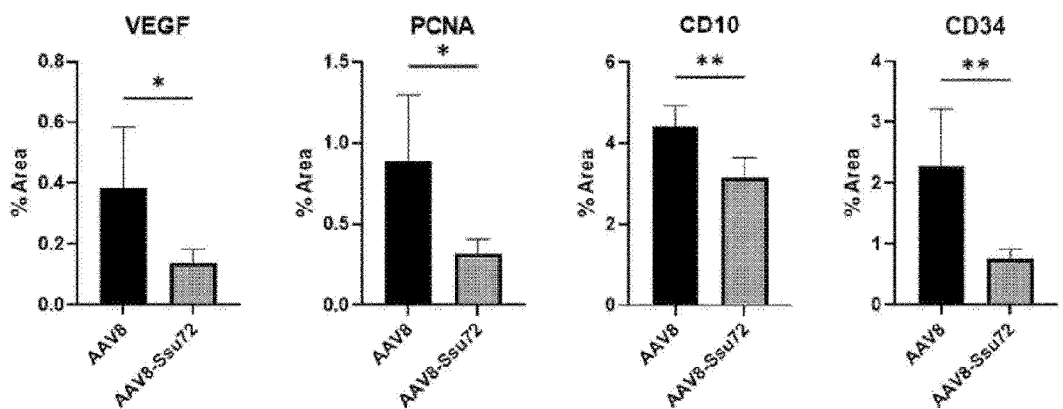

FIG. 9D shows a series of photographs representing appearance of livers and the results of IHC analysis for HCC-related proteins (VEGF, PCNA, CD10 and CD34) in the liver tissues after the experiment described in FIG. 9C (upper) and a series of graphs quantifying the results of the above IHC analysis (lower).

DETAILED DESCRIPTION

Definition of Terms

As used herein, the term "liver cancer" refers to a primary malignant tumor that occurs primarily in the liver. Cancer that has metastasized to the liver from other organs is also commonly called liver cancer, but strictly speaking, it refers only to primary cancer. Pathologically (or histologically), there are various types of primary liver cancers, such as hepatocellular carcinoma (HCC), cholangiocarcinoma, hepatoblastoma, and hemangiosarcoma.

As used herein, the term "primary liver cancer" is classified into hepatocellular carcinoma originating from hepatocytes and cholangiocarcinoma originating from epithelial cells of the hepatobiliary duct. In both of primary liver cancers, tumor cells proliferate and enlarge dysplastic nodules and destruct normal cells and cause jaundice and further metastasize to the peritoneum or lungs, leading to death.

As used herein, the term "secondary liver cancer" is a liver cancer that is caused by metastasis of cancer that occurs in other organs to the liver, and is reported clinically about twice as much as primary liver cancer. Secondary liver cancer mainly involves hepatogenous metastasis such as portal vein and hepatic artery and primary lesions include gastric cancer, rectal cancer, colorectal cancer, and other digestive cancers, pancreatic cancer, gallbladder cancer, lung cancer, breast cancer, and uterine cancer. Among them, metastasis from digestive cancer is the most frequent. Secondary liver cancer is often a multiple cancer, thus it is impossible to remove it by resection and chemotherapy is often used.

As used herein, the term "Ssu72" is known as a dephosphorylation enzyme that catalyzes dephosphorylation of the C-terminal domain of RNA polymerase II in a yeast model, but it's in vivo function is not well known in higher animals. The genes and proteins are all conserved from yeast to chimpanzees, dogs, pigs, mice, rats, and the like, and specific nucleotide sequences and protein information are known from NCBI (NCBI Reference Sequence: NM_026899.3, NM_200728.1, etc.).

DETAILED DESCRIPTION OF THE INVENTION

In an aspect of the present invention, there is provided a method for treating a patient suffering from liver cancer comprising administrating to the patient at least one selected from the group consisting of:

a Ssu72 peptide, a polynucleotide encoding the Ssu72 peptide, and an expression vector comprising the polynucleotide.

In the method, the Ssu72 peptide may have the amino acid sequence represented by SEQ ID NO: 1.

In the method, the Ssu72 peptide may be encoded by a polynucleotide having the nucleotide sequence represented by SEQ ID NO: 2.

In the method, the polynucleotide may be DNA or RNA.

In the method, the expression vector may be a viral vector or a non-viral vector.

In the method, the viral vector may be an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector. In a preferred embodiment, the viral vector may an adeno-associated virus (AAV) vector. In a more preferred embodiment, the AAV vector may be an AAV8 vector.

In the method, the non-viral vector may be a DNA vector, a nanoparticle, a cationic polymer, an exosome, an extracellular vesicle or a liposome.

In the method, the DNA vector may be a plasmid vector, a cosmid vector, a phagemid vector, or an artificial human chromosome.

In the method, the vector may comprise a gene construct in which the polynucleotide encoding the Ssu72 protein is operably linked to a promoter.

In the method, the promoter may be a constitutive promoter, an inducible promoter, or a liver-specific promoter. The constitutive promoter may be a CMV-HSV thymidine kinase promoter, a CMV promoter, an SV40 promoter, an RSV (Rous sarcoma virus) promoter, a human kidney urea 1α-promoter. The inducible promoter may be a glucocorticoid-inducible MMTV (Moloney mouse tumor virus) promoter, a metallothionein-inducible promoter, a tetracycline-inducible promoter. The liver-specific promoter may be a thyroxin-binding globulin (TBG) promoter, a PBGD promoter, an α-1 anti-trypsin promoter (EhAlbAAT), an Hepatic Control Region (HCR)-ApoCII hybrid promoter, an HCR-hAAT hybrid promoter, an apolipoprotein E (ApoE) promoter, a phosphoglycerate kinase [PGK] promoter, or a hybrid liver-specific promoter (HLP). In a preferred embodiment, the liver-specific promoter may be a thyroxin-binding globulin (TBG) promoter. The TBD promoter may comprises the nucleotide sequence of SEQ ID NO: 3.

In the method, the patient may show lower expression or activity of Ssu72 peptide in the cancer tissue than a normal subject's liver or non-cancer liver tissue of the patient.

In another aspect of the present invention, there is provided a method of predicting the likelihood of occurrence of liver cancer in a subject comprising:

measuring the expression level of Ssu72 or activity of the Ssu72 in a sample obtained from the subject; and determining that the subject is likely to develop nonalcoholic liver fatty disease (NASH)-derived hepatocellular carcinoma (HCC) when the expression level of Ssu72 is lower than that of a normal subject or normal tissues of the subject or the Ssu72 is expressed as an inactive form.

In the method, the Ssu72 peptide may have the amino acid sequence represented by SEQ ID NO: 1.

In the method, the Ssu72 peptide may be encoded by a polynucleotide having the nucleotide sequence represented by SEQ ID NO: 2.

In the method, the sample may be a liver tissue biopsy or a body fluid, and the body fluid may be saliva, blood, serum, plasma, urine, tears or sweat.

In another aspect of the present invention, there is provided a method of preventing liver cancer in a subject comprising:

administering Ssu72 peptide consisting of the amino acid sequence represented by SEQ ID NO: 1, a polynucleotide encoding the Ssu72 peptide, or an expression vector comprising the polynucleotide to the subject.

In the method, the Ssu72 peptide may be encoded by a polynucleotide having the nucleotide sequence represented by SEQ ID NO: 2.

In the method, the polynucleotide may be DNA or RNA.

In the method, the expression vector may be a viral vector or a non-viral vector.

In the method, the viral vector may be an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector. In a preferred embodiment, the viral vector may an adeno-associated virus (AAV) vector. In a more preferred embodiment, the AAV vector may be an AAV8 vector.

In the method, the non-viral vector may be a DNA vector, a nanoparticle, a cationic polymer, an exosome, an extracellular vesicle or a liposome.

In the method, the DNA vector may be a plasmid vector, a cosmid vector, a phagemid vector, or an artificial human chromosome.

In the method, the vector may comprise a gene construct in which the polynucleotide encoding the Ssu72 protein is operably linked to a promoter.

In the method, the promoter may be a constitutive promoter, an inducible promoter, or a liver-specific promoter. The constitutive promoter may be a CMV-HSV thymidine kinase promoter, a CMV promoter, an SV40 promoter, an RSV (Rous sarcoma virus) promoter, a human kidney urea 1α-promoter. The inducible promoter may be a glucocorticoid-inducible MMTV (Moloney mouse tumor virus) promoter, a metallothionein-inducible promoter, a tetracycline-inducible promoter. The liver-specific promoter may be a thyroxin-binding globulin (TBG) promoter, a PBGD promoter, an α-1 anti-trypsin promoter (EhAlbAAT), an Hepatic Control Region (HCR)-ApoCII hybrid promoter, an HCR-hAAT hybrid promoter, an apolipoprotein E (ApoE) promoter, a phosphoglycerate kinase [PGK] promoter, or a hybrid liver-specific promoter (HLP). In a preferred embodiment, the liver-specific promoter may be a thyroxin-binding globulin (TBG) promoter. The TBD promoter may comprises the nucleotide sequence of SEQ ID NO: 3.

In the method, the subject may show lower expression level of Ssu72 in the liver than a normal subject or the Ssu72 is expressed as an inactive form in the liver of the subject.

In another aspect of the present invention, there is provided a method of determining type of a liver cancer in a patient comprising:

measuring the expression level of Ssu72 or activity of the Ssu72 in a cancer tissue obtained from the patient; and determining that the liver cancer is NASH-derived hepatocellular carcinoma when the expression level of Ssu72 in the cancer tissue is lower than that of a normal subject or a normal liver tissue of the patient or the Ssu72 is expressed as an inactive form in the cancer tissue.

In the method, the Ssu72 peptide may have the amino acid sequence represented by SEQ ID NO: 1.

In the method, the Ssu72 peptide may be encoded by a polynucleotide having the nucleotide sequence represented by SEQ ID NO: 2.

Accordingly, in another aspect, there is provided a method of restoring the expression or function of HNF4α in hepatocytes of a subject suffering from hepatocellular carcinoma, comprising administering Ssu72 peptide or a polynucleotide encoding the same to the subject.

In the method, the sample may be a liver tissue biopsy or a body fluid, and the body fluid may be saliva, blood, urine, tears or sweat.

In another aspect of the present invention, there is provided a method of predicting the likelihood of occurrence of liver cancer in a subject comprising:

measuring the expression level of Ssu72 or activity of the Ssu72 in a sample obtained from the subject; and determining that the subject is likely to develop nonalcoholic liver fatty disease (NASH)-derived hepatocellular carcinoma (HCC) when the expression level of Ssu72 is lower than that of a normal subject or normal tissues of the subject or the Ssu72 is expressed as an inactive form.

In the method, the sample may be a liver tissue biopsy or a body fluid, and the body fluid may be saliva, blood, urine, tears or sweat.

In the method, the expression level or activity of an Ssu72 peptide may be measured by a process known in the art. The process may include an RT-PCR, an ELISA, a RIA (radioimmunoassay), a Western blot assay, a phosphatase activity assay. The phosphatase activity assay may be performed by using a C-terminal domain of RNA polymerase II as a substrate.

In another aspect of the present invention, there is provided a method of screening drug candidate for treating liver cancer comprising:

treating a candidate substance in the hepatocytes in culture or experimental animals except humans;

measuring the expression of Ssu4 or the interaction between the Ssu72 and HNF4α in the hepatocyte or the experimental animals; and selecting a candidate substance that increases the expression of Ssu72 or the interaction between Ssu72 and HNF4α in the hepatocytes or experimental animals.

In the method, the Ssu72 polypeptide having amino acid sequence represented by SEQ ID NO: 1 may be positioned on or into a drug delivery vehicle, and the drug delivery vehicle may include, for example, a nanoparticle, micelles, liposomes, lipid-derived vesicles, or exosomes.

In another aspect of the present invention, there is provided a recombinant AAV8 vector comprising a gene construct in which a polynucleotide encoding an Ssu72 peptide having the amino acid sequence represented by SEQ ID NO: 1 is operably linked to a TBG promoter having a polynucleotide sequence represented by SEQ ID NO: 3.

In another aspect of the present invention, there is provided a pharmaceutical composition for treating liver cancer comprising Ssu72 peptide consisting of the amino acid sequence represented by SEQ ID NO: 1, a polynucleotide encoding the Ssu72 peptide, or an expression vector comprising the polynucleotide as an active ingredient.

In another aspect of the present invention, there is provided a pharmaceutical composition for preventing liver cancer comprising Ssu72 peptide consisting of the amino acid sequence represented by SEQ ID NO: 1, a polynucleotide encoding the Ssu72 peptide, or an expression vector comprising the polynucleotide as an active ingredient.

In the present invention, the Ssu72 protein may be composed of the amino acid sequence represented by SEQ ID NO: 1. Alternatively, a peptide having at least 70%, preferably at least 80%, more preferably at least 90% homology with the amino acid sequence represented by SEQ ID NO: 1, most preferably a peptide having at least 95%, 96%, 97%, 98% or 99% sequence homology with the amino acid sequence represented by SEQ ID NO: 1 may be used if it has biological activity of Ssu72. In the present invention, the nucleotide encoding the Ssu72 protein may be composed of the nucleotide sequence represented by SEQ ID NO: 2.

In the pharmaceutical composition, the polynucleotide encoding the peptide may have a nucleic acid sequence represented by SEQ ID NO:2.

The vector comprising a polynucleotide encoding Ssu72 as an active ingredient may be used as a vaccine for preventing or treating HCC. In this case, the vector may be a viral or non-viral vector. The viral vector may be any one selected from the group consisting of adenovirus, adeno-associated virus (AAV), helper-dependent adenovirus and retroviral vectors, and the non-viral vector may be a plasmid, liposome, or the like. In this case, the adeno-associated virus may be AAV8 for liver-specific gene transfer, but is not limited thereto.

In the pharmaceutical composition, the expression vector may be a viral vector or a non-viral vector. The viral vector may be an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector. The non-viral vector may be a DNA vector, a nanoparticle, a cationic polymer, an exosome, an extracellular vesicle or a liposome. The DNA vector may be a plasmid vector, a cosmid vector, a phagemid vector, or an artificial human chromosome.

In the pharmaceutical composition, the liver cancer may be primary liver cancer or secondary liver cancer. The primary cancer may be hepatocellular carcinoma or cholangiocarcinoma.

The pharmaceutical composition of the present invention may include a recombinant vector alone or one or more pharmaceutically acceptable carriers, which contains a pharmaceutically effective amount of Ssu72 protein or a nucleotide encoding the Ssu72 protein, or a vector comprising the polynucleotide as an active ingredient. In this case, pharmaceutically acceptable carriers may be those commonly used in formulation, and may include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methylcellulose, methylhydroxybenzoate, propyl hydroxybenzoate, talc, magnesium stearate, and mineral oil. In addition, a lubricant, a wetting agent, a sweetening agent, a flavoring agent, an emulsifying agent, a suspending agent, a preservative, etc. may be additionally included in addition to the above components.

The pharmaceutical composition of the present invention may be administered parenterally (e.g, intravenously, subcutaneously, intraperitoneally or topically) according to a desired method, and although the dosage may vary depending on the condition and weight of the patient, the degree of disease, the drug formulation, administration route and time, it may be selected by those skilled in the art.

The pharmaceutical composition of the present invention is administered in a therapeutically effective amount. In the present invention, The "therapeutically effective amount" means an amount sufficient to treat a disease at a reasonable benefit/risk ratio applicable to medical treatment, and the therapeutically effective amount may vary according to the type and severity of the disease, drug activity, sensitivity to drugs, time of administration, route of administration and excretion rate of drugs, duration of treatment, factors including concomitant drugs, and other factors well known in the medical field. The pharmaceutical composition according to the present invention may be administered as an individual therapeutic agent or may be administered in combination with other therapeutic agents, may be administered sequentially or simultaneously with other conventional therapeutic agents, and may be administered as a single or multiple dose. Taking all of the above factors into consideration, it is important to administer an amount capable of obtaining the maximum effect with a minimum amount without side effects, which can be easily determined by those skilled in the art. Specifically, the therapeutically effective amount of the pharmaceutical composition of the present invention may vary depending on the age, sex, condition, weight of patients, absorption ratio of the active ingredient into the body, inactivation rate and excretion rate, disease type, and drugs used in combination, generally 1 to 500 mg per 1 kg of body weight may be administered daily or every other day, or divided into 1 to 3 times a day. However, since it may increase or decrease depending on the route of administration, sex, weight, age, etc., the dosage is not intended to limit the scope of the present invention in any way. In a preferred embodiment, where the vector is an AAV vector, the dosage of the vector may be from $1 \times 10^{10}$ gc/kg to $1 \times 10^{15}$ gc/kg or more, suitably from $1 \times 10^{12}$ gc/kg to $1 \times 10^{14}$ gc/kg, suitably from $5 \times 10^{12}$ gc/kg to $5 \times 10^{13}$ gc/kg.

In general, the subject in need thereof will be a mammal, and preferably primate, more preferably a human. Typically, the subject in need thereof will display symptoms characteristic of a disease. The method typically comprises ameliorating the symptoms displayed by the subject in need thereof, by expressing the therapeutic amount of the therapeutic product.

Gene therapy protocols for therapeutic gene expression in target cells in vitro and in vivo, are well-known in the art and will not be discussed in detail herein. Briefly, they include intramuscular injection, interstitial injection, instillation in airways, application to endothelium, intra-hepatic injection, intra-parenchymal injection or intravenous or intra-arterial administration (e.g. intra-hepatic artery, intra-hepatic vein) of plasmid DNA vectors (naked or in liposomes) or viral vectors. Various devices have been developed for enhancing the availability of DNA to the target cell. While a simple approach is to contact the target cell physically with catheters or implantable materials containing the relevant vector, more complex approaches can use jet injection devices or electroporators for the intramuscular gene transfer. Gene transfer into mammalian liver cells has been performed using both ex vivo and in vivo procedures. The ex vivo approach typically requires harvesting of the liver cells, in vitro transduction with suitable expression vectors, followed by reintroduction of the transduced hepatocytes the liver. In vivo gene transfer has been achieved by injecting the non-viral vectors or viral vectors into the liver parenchyma, hepatic artery, or portal vein.

In another aspect of the present invention, there is provided a method of determining type of a liver cancer in a patient comprising:

measuring the expression level of Ssu72 or activity of the Ssu72 in a sample obtained from the patient; and diagnosing that the liver cancer is NASH-derived hepatocellular carcinoma when the expression level of Ssu72 is lower than that of a normal subject or normal tissues of the patient or the Ssu72 is expressed as an inactive form.

In the method, the sample may be a liver tissue biopsy or a body fluid, and the body fluid may be saliva, blood, serum, plasma, urine, tears or sweat.

In an exemplary embodiment of the present invention, a gene construct was prepared so that the HA tag was included in the Ssu72 peptide consisting of the amino acid sequence represented by SEQ ID NO: 1. The reason to add the HA tag is to distinguish a recombinant Ssu72 protein expressed by transduction from inherent Ssu72 protein when performing analyses such as Western blotting analysis, since the Ssu72 protein expressed by gene transduction is indistinguishable from the endogenous Ssu72 protein in the body. Therefore, the actual gene construct for therapeutic or prophylactic use may include a tag for identification such as an HA tag, or it may be removed to minimize immunogenicity. The expression vector of the present invention may be any recombinant vector that is generally manufactured, may include both non-viral vectors and viral vectors, and preferably may be recombinant viral vectors, but is not limited thereto.

In the recombinant vector, the polynucleotide may be contained in a form of a gene construct operably linked to a regulatory sequence.

As used herein, the term "operably linked to" means that a target nucleic acid sequence (for example, in vitro transcription/translation system or in a host cell) is linked to the regulatory sequence in such a way that the target nucleic acid sequence can be expressed.

As used herein, the term "regulatory sequence" is meant to include a promoter, an enhancer, and other regulatory elements (for example, polyadenylation signal). Examples of the regulatory sequence include a sequence which directs such that a target nucleic acid is constantly expressed in many host cells, a sequence (for example, a tissue-specific regulatory sequence) which directs such that a target nucleic acid is expressed only in a specific tissue cell, and a sequence (for example, an inducible regulatory sequence) which directs such that expression is induced by a specific signal. Those skilled in the art could understand that the design of an expression vector may vary depending on factors such as the selection of a host cell to be transformed and the desired level of protein expression. The expression vector of the present invention can be introduced into a host cell to express the fusion protein. Regulatory sequences which enable expression in the eukaryotic cell and the prokaryotic cell are well known to those skilled in the art. As described above, these regulatory sequences generally include regulatory sequences responsible for transcription initiation, and optionally, a poly-A signal responsible for transcription termination and stabilization of a transcript. Additional regulatory sequences may include a translation enhancing factor and/or a naturally-combined or heterologous promoter region, in addition to the transcription regulatory factor. For example, possible regulatory sequences which enable expression in a mammalian host cell include a CMV-HSV thymidine kinase promoter, SV40, an RSV (Rous sarcoma virus)-promoter, a human kidney urea 1α-promoter, a glucocorticoid-inducing MMTV (Moloney mouse tumor virus)-promoter, a metallothionein- or tetracycline-inducible promoter, or an amplifying agent such as a CMV promoter and an SV40 promoter. It is considered that for expression in the liver, a liver-specific promoter, such as PBGD promoter, α-1 anti-trypsin promoter (EhAlbAAT), a thyroxin-binding globulin (TBG) promoter, an Hepatic Control Region (HCR)-ApoCII hybrid promoter, an HCR-hAAT hybrid promoter, an apolipoprotein E (ApoE) promoter, phosphoglycerate kinase [PGK] promoter, hybrid liver-specific promoter [HLP], or a liver-specific promoter disclosed in prior arts (WO2001098482A; WO2020104782A) can be used. The abovementioned promoters are known in the art, and are described in the literature (Charron, *J. Biol. Chem.* 270: 25739-25745, 1995). For the expression in the prokaryotic cell, a number of promoters, including a lac-promoter, a tac-promoter, or a trp promoter, have been disclosed. In addition to the factors capable of initiating transcription, the regulatory sequences may include a transcription termination signal, such as an SV40-poly-A site and a TK-poly-A site, on the downstream of the polynucleotide according to one exemplary embodiment of the present invention. In the present specification, suitable expression vectors are known in the art, and examples thereof include Okayama-Berg cDNA expression vector pcDV1 (Parmacia), pRc/CMV, pcDNA1, pcDNA3 (Invitrogen), pSPORT1 (GIBCO BRL), pGX-27 (Korean Patent No. 1442254), pX (Pagano et al., *Science* 255: 1144-1147, 1992), a yeast two-hybrid vector such as pEG202 and dpJG4-5 (Gyuris et al., *Cell* 75: 791-803, 1995), and a prokaryotic expression vector such as lambda gt11 and pGEX (Amersham Pharmacia). The vector may further include a polynucleotide encoding a secretion signal, in addition to the nucleic acid molecules of the present invention. The secretion signals are well known to those skilled in the art. Moreover, depending on the used expression system, a leader sequence which can lead the fusion protein according to one exemplary embodiment of the present invention to a cellular compartment is combined with a coding sequence of the polynucleotide according to one exemplary embodiment of the present invention, and is preferably a leader sequence capable of directly secreting a decoded protein or the protein thereof into a pericytoplasmic or extracellular medium.

In the composition according to an embodiment of the present invention, the regulatory sequence may exhibit systemic expression or tissue-specific expression pattern, and in the case of tissue-specific expression, it may exhibit liver-specific expression pattern. In this case, a liver-specific regulatory sequence such as the TBG promoter (SEQ ID NO: 3) may be used in order to exhibit a liver-specific expression pattern, but is not limited thereto.

In addition, the vector of the present invention can be prepared, for example, by a standard recombinant DNA technique, and examples of the standard recombinant DNA technique include ligation of a smooth terminus and an adhesion terminus, a restriction enzyme treatment to provide a proper terminus, removal of a phosphate group by an alkaline phosphatase treatment to prevent inappropriate binding, and enzymatic linkage by T4 DNA ligase. The vector of the present invention can be prepared by recombining DNA encoding a signal peptide obtained by chemical synthesis or a genetic recombination technique, and a polynucleotide encoding the Ssu72 peptide according to one exemplary embodiment of the present invention, with a vector containing an appropriate regulatory sequence. The vector containing a regulatory sequence can be commercially purchased or prepared.

The expression vector may further include a polynucleotide encoding a secretion signal sequence, and the secretion signal sequence induces the extracellular secretion of the recombinant protein expressed in the cell, and may be a tissue plasminogen activator (tPA) signal sequence, a herpes simplex virus glycoprotein Ds (HSV gDs) signal sequence, or a growth hormone signal sequence.

The expression vector according to one exemplary embodiment of the present invention may be an expression vector capable of expressing the protein in a host cell, and the expression vector may be in any form such as a plasmid vector, a viral vector, a cosmid vector, a phagemid vector, or an artificial human chromosome.

The present inventors confirmed that it is possible to treat liver cancer derived from NASH or chronic chemical stimulation-induced liver cancer through a pharmaceutical composition including a polynucleotide encoding Ssu72. The present inventors identified the function of Ssu72 that regulates chromosome integrity, which is important for differentiation and function of hepatocytes at first. In addition, the present inventors reported that hepatocyte-specific Ssu72 gene deficiencies in mouse models cause NAFLD and NASH (Se-Hyuk Kim et al., *Heptol.* 63:247-259, 2016; KR10-2016-0054719A). Subsequently, the present inventors investigated that Ssu72 can also influence functional regulation of hepatocytes by confirming the relationship of down-regulation of Ssu72 with onset of hepatocellular carcinoma or malignant hepatocellular carcinoma and the correlation between HNF4α, which is a key transcriptional factor for the regulation of normal function of hepatocytes and Ssu72 from the analyses using liver cancer model mice and clinical liver biopsies of HCC patients. Based on the finding, the present inventors prepared a pharmaceutical compositions containing Ssu72 and confirmed that the therapeutic effect of the composition for the treatment liver cancer in feed-induced liver cancer model mice and chemical-induced liver cancer model mice. Thus, the pharmaceutical composition can be used for the manufacture of a therapeutic agent for the treatment of liver cancer in human.

Liver cancer has a wide variety of causes, such as genetic factors, non-genetic factors, viral infection, alcohol, smoking, diet, drugs, and stress, and it occurs when a complex signaling system between parenchymal cells such as hepatocytes constituting the liver and non-parenchymal cells such as hepatic stellate cells and immune cells constituting the liver microenvironment is affected for a long time due to the above causes. Therefore, if a specific liver cancer-related gene is defective, it can often be confirmed that abnormal or suppressed expression of the gene causes liver cancer. However in the treatment of liver cancer, it is very difficult to expect to treat liver cancer by preparing a pharmaceutical composition comprising only a single particular gene. This is why it is difficult to predict the mode of action through the pathogenesis of liver cancer caused by various factors over a long period of time. The present inventors identified the pathogenesis of liver cancer due to Ssu72 defects, and the epidemiological relationship between HNF4α and Ssu72 in the occurrence of liver cancer. In addition, the present inventors prepared a pharmaceutical composition comprising Ssu72 and confirmed therapeutic effect of the composition on the treatment of liver cancer based on the discovery. The present invention is drawn to a therapeutic agent for treating liver cancer having discriminate merits capable of treating chronic liver cancer only using a gene encoding Ssu72 or an Ssu72 protein and showing therapeutic effect through a mechanism of action inducing Ssu72 in the hepatocellular carcinoma animal model.

Recently, molecular targeting therapeutics have emerged that have fewer side effects and can expect more effective results by selectively attacking only specific targets using various characteristics of cancer cells. Among them, Sorafenib is a representative oral anticancer drug frequently used in progressive kidney cancer and liver cancer, which is a multiple kinase inhibitor blocking various tumor-related signaling pathways and receptors related to angiogenesis factors through the inhibition of tyrosine protein kinases and Raf kinase. In recent years, it has been known to have some effect on non-reactive thyroid cancer, lung squamous cell carcinoma, and recurrent neuroblastoma, but various side effects such as skin rash, hand-foot skin reactions, diarrhea, hypertension, and reversible posterior brain disease syndrome, etc. have been reported in clinical trials and hypersensitive reactions for Sorafenib have been reported. In addition, it was reported that dexamethasone, ketoconazole, rifampin and doxorubicin affect liver microsomal enzymes, or drugs metabolized by the liver microsomal enzymes or exhibit detrimental reactions with drugs metabolized by uridine diphosphate-glucuronosyltransferase (UGT) enzymes. As a result, the types and usage of molecular targeting therapeutics that have provided a breakthrough in the treatment of liver cancer are expected to increase worldwide, but various molecular targeting therapeutics have not been developed due to lack of discovery of genes for molecular targeting and pre-clinical research models.

Under the background, the present inventors investigated the therapeutic effects and antiviral effects of Ssu72 gene on fatty liver, hepatitis, and liver fibrosis and finally developed a therapeutic agent for treating liver cancer comprising Ssu72 protein or a polynucleotide encoding the Ssu72 protein capable of treating hepatocellular carcinoma as well as preventing liver damage and liver fibrosis with high sensitivity and specificity without side effects through in vivo experiments.

Specifically, the present inventors cloned a polynucleotide encoding Ssu72 protein and inserted a polynucleotide into pCMV vector after treating BamHI and XbaI restriction enzymes in order to construct pCMV.HA-Ssu72. In addition, the present inventors constructed AAV8.TBG.HA-Ssu72 viral vector (hereinafter referred to as "AAV8 Ssu72") by removing a polynucleotide encoding Cre from AAV.TBG-.PI.Cre,rBG vector (Addgene, USA) and inserting a polynucleotide encoding HA-Ssu72 derived from the pCMV.HA-Ssu72 into the AAV.TBG.PI.Cre.rBG vector treated with ClaI and SalI restriction enzymes in order to construct a viral vector, AAV8 vector expressing Ssu72. Thereafter, the effect of relieving and treating liver cancer was verified using the prepared vector. In addition, it was confirmed the function of Ssu72 in liver cancer by applying two models that can cause liver cancer to mice lacking Ssu72 and normal mice. First, using chemical-induced HCC model mice through diethyl nitrosamine (DEN) administration, onset and the progression of liver cancer was confirmed and probability of treating liver cancer of Ssu72 was investigated and second, using STAM model mice in which Streptozotocin (STZ) was administered at 2 days of age and fed high fat diet at 4 weeks of age, onset of liver cancer and the degree of fibrosis were compared. Based on the above results, the normal mice to which STAM model was applied was administrated with AAV8 Ssu72 and the occurrence and severity of liver diseases were evaluated. As a result, In the AAV8 Ssu72-administered group, significant therapeutic effects were confirmed for steatohepatitis, liver fibrosis, liver nodule, liver weight increase, and liver level increase observed in the immediate stage of liver cancer.

In addition, to confirm the molecular mechanism of Ssu72 in the transition of fatty liver to HCC, omics analysis was performed. As a result, it was confirmed that 45% of genes downregulated in Ssu72$^{\Delta hep}$ hepatocytes genetically modified to be deficient in liver expression of Ssu72 gene were target genes of HNF4α, a transcription factor. Based on these results, the correlation between Ssu72 and HNF4α expression was further analyzed using clinical samples of HCC patients and steatohepatitis patients and/or cirrhosis patients, and it was confirmed that the expression of Ssu72 and HNF4α was significantly lowered in HCC patients, positive correlation between Ssu72 and HNF4α in the steatohepatitis patients and/or liver fibrosis patients. In addition, it was confirmed that Ssu72 forms a complex with hyperphosphorylated HNF4α in hepatocytes, and deficiency of Ssu72 in hepatocytes induces the maintenance of HNF4α under liver toxicity conditions, thereby reducing the transcription activity of HNF4α. In addition, it was confirmed that hyperphosphorylation of HNF4α is reduced when Ssu72 gene is heterogeneously transduced in Ssu72$^{\Delta hep}$ hepatocytes and it is possible to recover the function of deactivated HNF4α by hyperphosphorylation or whose expression is reduced by administering Ssu72 or a polynucleotide encoding the Ssu72 to a subject. Thus, the Ssu72 protein or a polynucleotide encoding the same according to an embodiment of the present invention may be useful for treating these diseases by reversing NASH or liver fibrosis and diminished function of HNF4α closely related to development of HCC in this pathological state.

EXAMPLES

Hereinafter, the present invention will be described in more detail through following examples. However, the present invention is not limited to the examples disclosed below, can be implemented in various different forms. The examples are provided in order to fully disclose the present invention and fully inform those of ordinary skill in the art the scope of the present invention.

Example 1: Experimental Preparation

All animal experiments used in the present invention were performed according to guidelines of Association for Assessment and Accreditation of Laboratory Animal Care International (AAALAC International) and Institute of Laboratory Animal Resources (ILAR) which were approved by the Institutional Animal Care and Use Committee of Sungkyunkwan University School of Medicine (SUSM).

Figure 1:
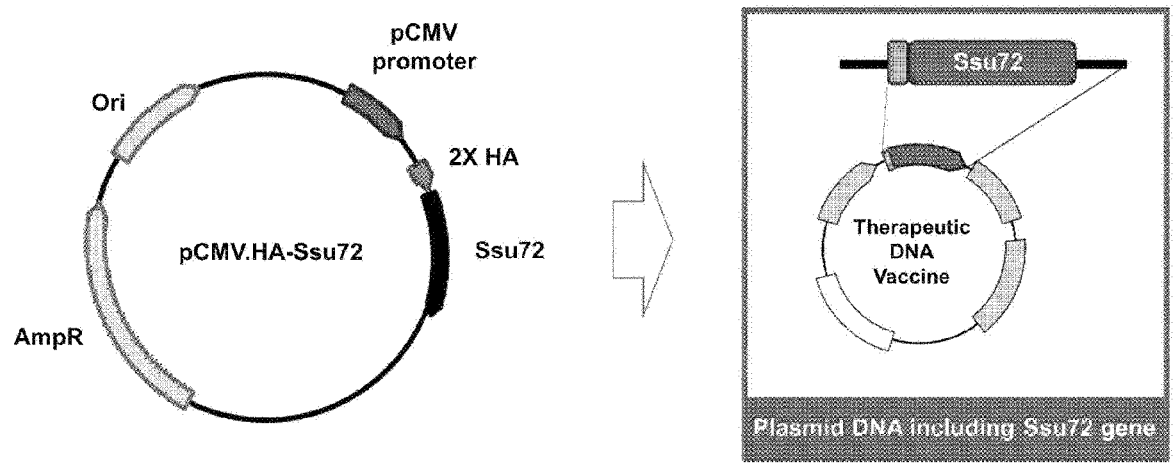

Example 2: Construction of Expression Vector Containing Polynucleotides Encoding Ssu72 Protein 2-1: pCMV.HA-Ssu72 Plasmid Vector Construction The present inventors cloned the polynucleotide encoding Ssu72 (SEQ ID NO: 2) through PCR to construct a therapeutic non-viral pCMV vector expressing Ssu72, after treating the amplified polynucleotide with BamHI and XbaI restriction enzymes, and then inserting into the digested polynucleotide fragment into pCMV.HA vector (Clonetech, USA) and designated the constructed recombinant vector as "pCMV.HA-Ssu72" (FIG. 1).

2-2: AAV8.TBG.HA-Ssu72 (AAV8 Ssu72) Vector Construction

Figure 2:
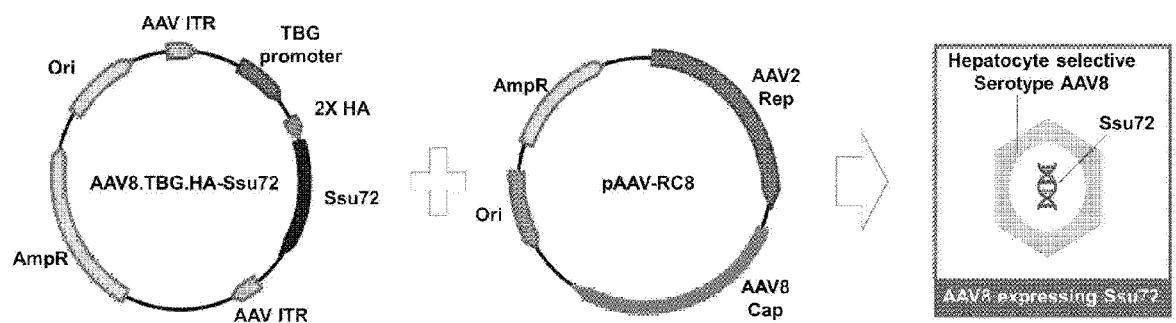

In order to construct an AAV8 vector expressing Ssu72, the present inventors transferred the polynucleotide encoding HA-Ssu72 excised from the pCMV.HA-Ssu72 vector prepared in Example 2-1 to the pAAV.TBG.PI.Cre.rBG vector (Addgene, USA) by removing a polynucleotide encoding Cre moiety form the pAAV.TBG.PI.Cre.rBG vector and inserting the excised polynucleotide to the pAAV.TBG.PI.Cre.rBG vector after digestion with ClaI and SalI restriction enzymes. The constructed vector was designated as "AAV8.TBG.HA-Ssu72 (AAV8 Ssu72)" (FIG. 2).

2-3: AAV8.TBG.HA-Ssu72 (AAV8 Ssu72) Virus Production

The present inventors prepared AAVs using the plasmid DNA obtained in Example 2-2. Specifically, to prepare the AAV, 293T cells were prepared the day before and stabilized for 24 hours, and the plasmid DNA prepared in Example 2-2 and pHelper and pAAV-RC8 (Agilent, USA), which are plasmids necessary for AAV production, added to the cells and the cells were transfected with the plasmids. The AAVs were obtained 3 to 4 days after transfection, and the prepared AAVs were quantified using a titration kit (AAVpro Titration Kit, Takara, Japan).

Example 3: Analysis of Ssu72 Protein Expression Level

Figure 3:
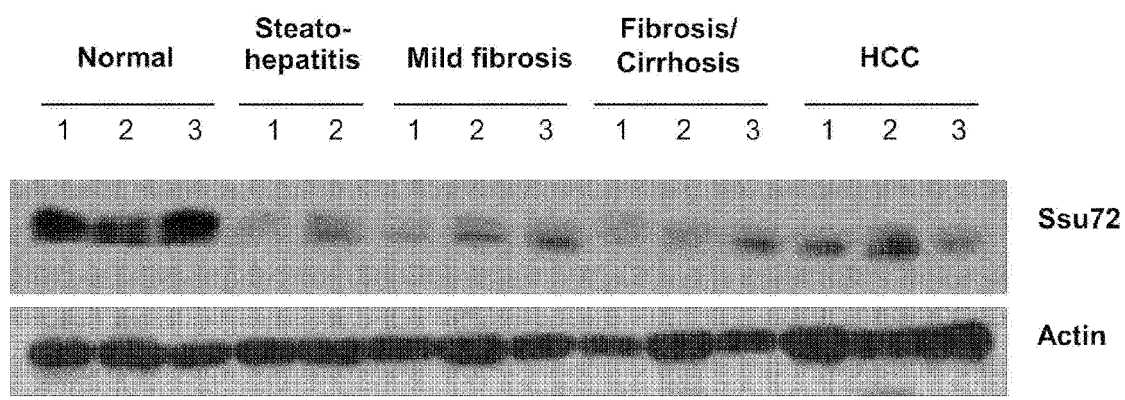
FIG. 3 is the result of immunoblotting showing the expression level of Ssu72 protein in liver tissue samples from normal human subject and liver tissue samples from patients suffering from steatohepatitis, mild liver fibrosis, cirrhosis and hepatocellular carcinoma (HCC), respectively through western blot analysis.

The present inventors investigated changes in the expression level of Ssu72 protein in the liver when liver diseases occur. Specifically, protein analysis was performed using liver biopsy tissues from healthy subjects and from patients suffering from steatohepatitis, liver fibrosis, fibrosis/cirrhosis, or hepatocellular carcinoma (HCC). As a result, it was confirmed that the expression level of Ssu72 was remarkably high in the liver of healthy subjects, and that Ssu72 expression was suppressed in the livers of patients suffering from liver diseases (FIG. 3). The above results suggest that there is a correlation between decreased expression level of Ssu72 and liver diseases.

Example 4: Observation of Changes in the Occurrence of Hepatocelluar Carcinoma According to the Suppression of Ssu72

Figure 4A:
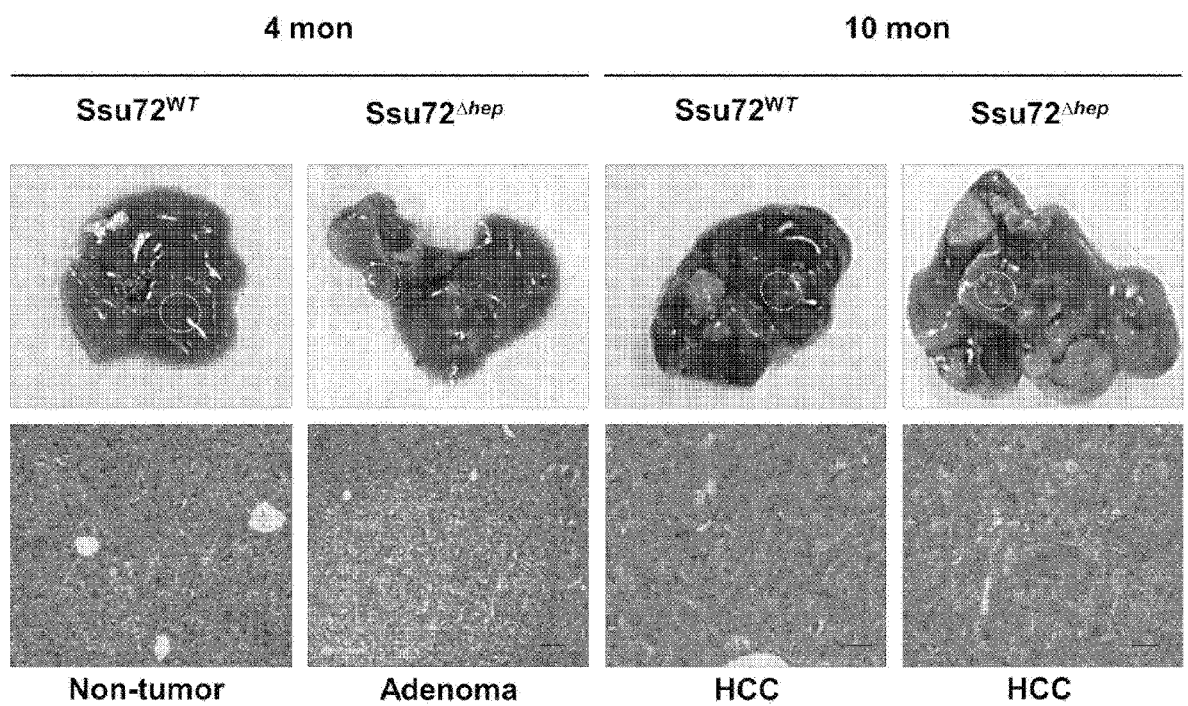
FIG. 4A shows appearances (upper panel) and internal structure (lower panel) of liver tissues of the wild type mice (Ssu72$^{WT}$), as a control group and liver-specific Ssu72-deficient mice (Ssu72$^{\Delta hep}$ after 4 months and 10 months from inducing hepatocellular carcinoma (HCC) by treating diethyl nitrosamine (DEN).
Figure 4B:
FIG. 4B is a series of graphs showing the results of analyzing the number of adenomas (left), the number of tumor nodules (center), and the size of tumors (right) after excising livers 10 months after DEN treatment from the Ssu72$^{WT}$ (◇) and Ssu72$^{\Delta hep}$ (◆) mice.
Figure 4C:
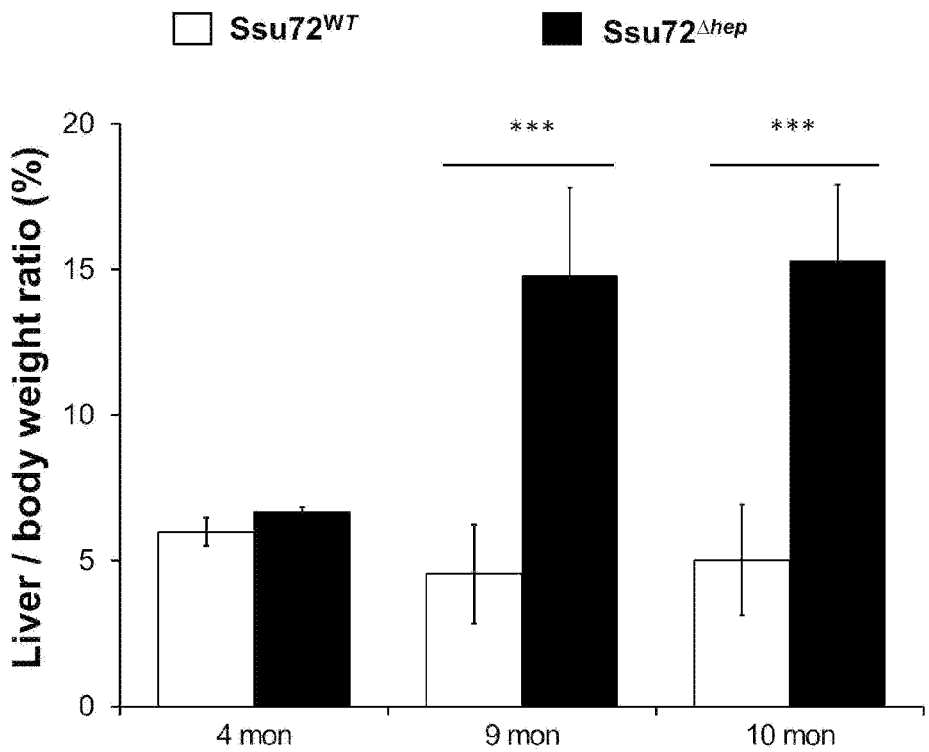
FIG. 4C is a graph showing the results of analyzing the body weight-to-liver weight ratio by measuring the body weight and the weight of the liver excised 4, 9 and 10 months after DEN treatment in the Ssu72$^{WT}$ (□) and Ssu72$^{\Delta hep}$ (■) mice, respectively.

In order to determine whether or not the susceptibility to liver cancer is increased according to the suppression of Ssu72 expression, the present inventors performed a histological analysis of liver tissues excised from liver-specific Ssu72-deficient mice (Ssu72$^{\Delta hep}$) and wild-type mice (Ssu72$^{WT}$) as a control group treated diethyl nitrosamine (DEN) in order to induce hepatocellular carcinoma after 4 months and 10 months from the treatment of DEN. As a result, it was confirmed that more nodules and larger liver cancer were generated on the liver surface of the liver-specific Ssu72-deficient mice (Ssu72$^{\Delta hep}$) than wild-type mice (FIG. 4A). As a result of performing liver biopsy tissue analysis through H&E staining after excising liver tissues from the experimental animals, adenomas were found in the livers excised from Ssu72$^{\Delta hep}$ mice 4 months from the induction of carcinogenesis, whereas the livers excised from Ssu72$^{WT}$ mice showed normal phenotypes. Although tumors occurred in Ssu72$^{WT}$ at 10 months from the induction of carcinogenesis, the size and number of tumors generated in Ssu72$^{\Delta hep}$ were significantly higher than those of Ssu72$^{WT}$ (FIG. 4B). Subsequently, as a result of H&E staining for tissue structure analysis, adenomas began to appear in the Ssu72$^{\Delta hep}$ liver at 4 months from the induction of liver cancer, and more severe liver cancer was observed in the livers of Ssu72$^{\Delta hep}$ mice than Ssu72$^{WT}$ at 10 months from the induction of liver cancer. In addition, as a result of measuring the liver weight-to-body weight ratio by excising livers from liver carcinogenesis-induced mice by DEN treatment, the liver weight-to-body weight ratios of Ssu72$^{WT}$ and Ssu72$^{\Delta hep}$ mice showed a similar pattern until 4 months from the induction of carcinogenesis. At 9 months and 10 months, it was confirmed that the liver weight-to-body weight ratio of Ssu72$^{\Delta hep}$ mice significantly increased (FIG. 4C).

Figure 4D:
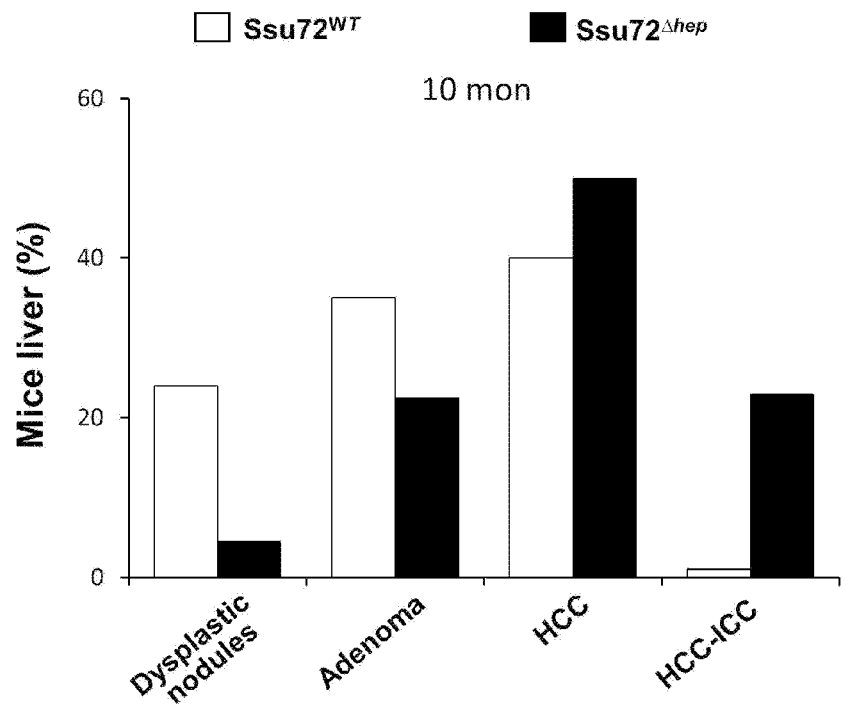
FIG. 4D shows the occurrence ratio of dysplastic nodules, adenoma, hepatocellular carcinoma (HCC), and intrahepatic cholangiocarcinoma (HCC-ICC), through structural analysis and histochemical analysis 10 months after DEN treatment in the Ssu72$^{WT}$ (□) and Ssu72$^{\Delta hep}$ (■) mice, respectively.

In addition, as a result of comparing the occurrence rates of liver cancer-related phenotypes in the livers of the Ssu72$^{WT}$ and Ssu72$^{\Delta hep}$ mice at 10 months from the induction of carcinogenesis, in the hepatocellular carcinoma model administered with DEN, liver diseases worsened in the order of dysplastic nodules, adenomas, and HCC. In terms of the occurrence rates of dysplastic nodules, adenomas, hepatocellular carcinoma (HCC) and intrahepatic cholangiocarcinoma (ICC), Ssu72$^{WT}$ had a high ratio of dysplastic nodules and adenomas, whereas Ssu72$^{\Delta hep}$ had the highest ratio of hepatocellular carcinomas. In particular, it was found that intrahepatic cholangiocarcinoma (HCC-ICC), which was hardly seen in Ssu72$^{WT}$, also occurred (FIG. 4D). These results suggest that the deficiency of Ssu72 increases the rate and severity of HCC and HCC-ICC.

Example 5: Comparison of Non-Alcoholic Steatohepatitis (NASH) Progression According to the Suppression of Ssu72

The present inventors investigated whether non-alcoholic steatohepatitis (NASH) worsened due to Ssu72 deficiency. Specifically, a STAM model that induces fibrosis and liver cancer was prepared by injecting Streptozotocin when the mice were 2 days old and feeding them a high-fat diet (HFD) from 4 weeks of age. If the duration of the STAM model is prolonged, severe HCC can also be induced, but the occurrence of NASH and liver cancer can be simultaneously observed by controlling the timing of sacrifice. After applying the STAM model to Ssu72$^{WT}$ and Ssu72$^{\Delta hep}$, the present inventors observed adenomas and nodules on the surface of livers at 4 months of age.

As a result, in the Ssu72$^{WT}$ mice, the number of adenomas and nodules on the surface of livers was small and the severity was low, whereas in the Ssu72$^{\Delta hep}$ mice, the number of nodules was high and the fat content was high in the tissue structure, and a cluster of inflammatory cells was observed, indicating that NASH was induced (FIG. 5A). In addition, as a result of measuring the number and size of tumors and nodules by analyzing the liver tissue and surface thereof, it was found that both the number and size of tumors and nodules were increased in the Ssu72$^{\Delta hep}$ mice compared to the Ssu72$^{WT}$ mice. In addition, NFALD activity score (NAS) was measured to determine the severity of NASH. NAS in the Ssu72$^{\Delta hep}$ mice was increased about 5 times compared to Ssu72$^{WT}$ mice and as a result of measuring the fibrosis index based on the fibrosis area, the fibrosis index was also increased by about 4 times in the Ssu72$^{\Delta hep}$ mice compared to the Ssu72$^{WT}$ mice (FIG. 5B).

Example 6: Analysis of Changes in Omics According to the Suppression of Ssu72 and Study of Mechanisms Involved The present inventors performed gene expression analysis using RNA-Seq on liver cells isolated from DEN-treated Ssu72$^{WT}$ and Ssu72$^{\Delta hep}$ mice to understand the potential mechanism underlying the increased liver dedifferentiation potential due to Ssu72 depletion after liver damage. According to heatmap analysis, expression levels of hepatocyte- and biliary-marker gene subsets were significantly downregulated in the hepatocytes from DEN-treated Ssu72$^{\Delta hep}$ mice compared to the hepatocytes form DEN-treated Ssu72$^{WT}$ mice, whereas progenitor genes were dramatically upregulated in the hepatocytes from DEN-treated Ssu72$^{\Delta hep}$ mice (FIG. 6A). The change in gene expression between hepatocytes from DEN-treated Ssu72$^{WT}$ mice and DEN-treated Ssu72$^{\Delta hep}$ were grouped by function through DAVID and items with high reliability were compared each other. As a result, in the hepatocytes from DEN-treated Ssu72$^{\Delta hep}$ mice, genes related to intrinsic physiological features of hepatocytes such as metabolic process of lipid, cholesterol and retinol and mitochondria, peroxisome and oxidative phosphorylation were downregulated. This suggests a potential role for Ssu72 in the intrinsic physiological features of hepatocytes, and demonstrates that Ssu72 is essential for maintaining intrinsic functions of hepatocytes (FIG. 6B). On the other hand, cell cycle-related gene subsets were aberrantly upregulated in the hepatocytes from DEN-treated Ssu72$^{\Delta hep}$ mice, suggesting that hepatocytes restore their proliferation potential by being dedifferentiated due to Ssu72 depletion in response to liver damage.

In addition, the present inventors discovered that about 45% of downregulated gene subsets in Ssu72$^{\Delta hep}$ hepatocytes belonged to target genes of HNF4α which is a critical transcription factor for maintenance of hepatocyte function (FIG. 6C). Moreover, about 39% of the gene subset whose expression was upregulated in the Ssu72$^{\Delta hep}$ hepatocytes belong to target genes of E2F, indicating deficiency of Ssu72 contributes to recovery of proliferative capacity through damage-mediated degeneration (Hyun Soo Kim et al., Cell Death & Differentiation Epub, 2021). Furthermore, it was shown that the deficiency of Ssu72 tends to downregulate four HNF4α targeting genes, Aadat, Fabp1, Grb7 and F10 through qRT-PCT analysis (FIG. 6D). In order to investigate the clinical relevance between Ssu72 and HNF4α expression, the present inventors evaluated the protein expression level of paired tissues obtained from 28 NASH-associated HCC patients by immunohistochemical staining. As a result, HCC patient whose expression of Ssu72 was weak showed low expression of HNF4α in the same tissue and vice versa. The correlation between Ssu72 and HNF4α expression was further analyzed in patients with NASH and/or cirrhosis and a close positive correlation between Ssu72 and HNF4α expression was found in patients with steatohepatitis, mild fibrosis or fibrosis/cirrhosis (FIG. 6E).

Furthermore, human liver tissue biopsies were obtained and the expression levels of Ssu72 and HNF4α were compared. When relative levels of Ssu72 and HNF4α mRNA in the liver biopsy samples from patients with steatohepatitis (n=12), mild fibrosis (n=70), or fibrosis/cirrhosis (n=105) and normal subjects (no diagnostic abnormalities, n=10) were analyzed, a close positive correlation between Ssu72 and HNF4α expression was also confirmed (FIG. 6F).

These results suggest that hepatic Ssu72 regulates HNF4α-mediated transcriptional signaling in response to liver damage, as Ssu72 is potentially highly downregulated in NASH and HCC patients through association with HNF4α expression.

Example 7: Modulation of HNF4α Phosphorylation and Activity by Ssu72

HNF4α is a master transcriptional factor related to maintenance of liver functions and is significantly downregulated in NASH, ASH, cirrhosis, and hepatoma occurrence. In particular, the transcriptional activity of HNF4α is mainly regulated by phosphorylation modification. In liver damage, the activity of several kinases such as AMPK, MAPK and PKA can induce hyperphosphorylation of HNF4α, thereby reducing its transcriptional activity. Accordingly, the present inventors investigated the phosphorylation level after DEN treatment in experimental mice to confirm the relationship between HNF4α and Ssu72.

As a result, DEN significantly induced phosphorylation of HNF4α evidenced by a change in mobility in the phospho-tag gel for hepatocytes of Ssu72$^{WT}$ mice, and the hyperphosphorylation of HNF4α was partially restored within 5 days after DEN administration in the liver from Ssu72$^{WT}$ mice. In addition, the hyperphosphorylated form of HNF4α in the liver of DEN-treated Ssu72$^{\Delta hep}$ mice was maintained continuously 5 days after DEN administration without activation of kinases such as AMPKα, which are known to phosphorylate Ser$^{304}$ of HNF4α during liver damage (FIG. 7A). IHC analysis also revealed that HNF4α was hyperphosphorylated in the liver of DEN-treated Ssu72$^{\Delta hep}$ mice (FIG. 7B). The above results suggest that Ssu72 may contribute to the dephosphorylation (or hypophosphorylation) of HNF4α due to liver damage by increasing the likelihood of directly responding to the hyperphosphorylation of HNF4α. In addition, to confirm the relationship between Ssu72 and HNF4α, an immunoprecipitation analysis was performed to investigate whether Ssu72 could physically bind to HNF4α. As a result, it was found that Ssu72 interacts with HNF4α under the condition of DEN-induced damage, which indicates that Ssu72 interacts with HNF4α. This suggests that Ssu72 can form a complex with hyperphosphorylated HNF4α selectively (FIG. 7C). Moreover, considering that Ssu72 deficiency affects the activity of HNF4α by maintaining hyperphosphorylated state of HNF4α, hepatocytes from floxed mice were isolated and the hepatocytes were transduced with a reporter gene construct comprising Tfr2 promoter which contains HNF4α binding motif in order to investigate the transcriptional activity of HNF4α after liver damage. Then, the hepatocytes were infected with adenovirus containing polynucleotides encoding Cre (Ad-Cre) and control (Ad-GFP) and 500 μM palmitic acid was administered to induce liver damage for 6 hours. As a result, the transcriptional activity of HNF4α in hepatocytes in which Ssu72 was normally present was slightly decreased due to liver damage, whereas the activity of hepatocytes in which Ssu72 was deficient was significantly reduced by the deficiency of Ssu72 (FIG. 7D).

The above results show that Ssu72-HNF4α signaling has an important function in regulating oncogenic liver dedifferentiation, and Ssu72 negatively regulates hepatocellular oncogenic proliferation and dedifferentiation by activating HNF4α-mediated transcription. Therefore, it is suggested that the Ssu72 can be used as a therapeutic agent for treating NASH-associated HCC Example 8: Verification of Prophylaxis and Treatment of Liver Diseases in STAM Model (Streptozotocin-High Fat Diet Model)

8-1: Validation of Therapeutic Effect Through Induction of Ssu72 Expression

The present inventors verified the effect of Ssu72 on liver diseases by AAV8 Ssu72 administration. Specifically, in early NASH, fatty liver is a typical symptom, so dietary control is recommended and effective in many cases. However, it is difficult to treat severe NASH with only dietary control because fibrosis including fatty liver has progressed. Such severe NASH can develop into liver cancer, and since there is no precaution against liver cancer caused by the hepatitis B virus, there is an urgent need to develop a method of treating and a therapeutic agent for treating severe NASH. Therefore, for the effective treatment of severe NASH, the treatment of fibrosis is important, and this criterion can be an indicator to determine the possibility of preventing liver cancer. In normal mice to which the STAM model is applied, fatty liver occurs at 6 weeks of age, NASH and early fibrosis appear at 8 weeks of age, and fibrosis becomes severe at 12 weeks of age. AAV8 Ssu72 of the present invention and AAV8 GFP as a control group were administered to 8-week-old STAM model mice, through the tail vein ($3 \times 10^{10}$ gc/g), and the mice were sacrificed 4 weeks later to compare structural differences within tissues through H&E staining.

As a result, in the control group, mice administered with AAV8 GFP, fatty liver was confirmed and severe liver damage was observed, whereas mice administered with AAV8 Ssu72 showed less fat distribution, smaller fat size, and significantly fewer damaged areas compared to the control group (FIG. 8A)

8-2: Comparison of Inhibitory Efficacy Against Liver Fibrosis

The present inventors performed Sirius red staining to evaluate whether inhibition of fibrosis through AAV8 Ssu72 administration. Specifically, AAV8 Ssu72 of the present invention and AAV8 GFP as a control group were administrated to STAM model mice through the tail vein ($3 \times 10^{10}$ gc/g), and 4 weeks later, the mice were sacrificed and collagen I/III were stained with Sirius red staining in order to determining the location and amount of collagen deposition generated through fibrosis reaction in the liver.

As a result, the liver tissue of the mice administered with AAV8 GFP showed a light brown color on the surface, and in the Sirius red staining, the central vein and the portal vein were stained with strong red, and at the same time, it was observed that stained sites between two veins were connected each other indicating that the fat content was high (FIG. 8B). However, the liver tissue of the mice administered with AAV8 Ssu72 according to an embodiment of the present invention was dark reddish-brown, and almost no fat accumulation was seen in the tissues. Similar to the mice administered with AAV8 GFP, the central vein and the portal vein periphery were strongly stained with Sirius red, but no connection between the two stained sites were observed. The above results suggest that liver fibrosis was inhibited by administration of AAV8 Ssu72 compared to the control group.

8-3: Analysis of Relief of Liver Damage

The present inventors performed the serochemical analysis, liver weight to body weight, and area ratio of tissue stained with Sirius red using liver and blood of STAM model mice administered with AAV8 GFP or AAV8 Ssu72. The liver weight-to-body weight is an indicator for measuring the degree of liver hypertrophy caused by liver damage, fibrosis, fatty liver, etc., and AST and ALT levels are indicators of liver damage because they are concentration of enzymes detected in the blood when liver damage occurs.

As a result, it was found that all three levels were significantly decreased in the mice administered with AAV8 Ssu72 compared to the mice administered with AAV8 GFP. In addition, as a result of measuring Sirius red-positive area, it was also observed that the area treated with AAV8 Ssu72 was significantly reduced (FIG. 8C). Therefore, the above results suggest that the AAV8 Ssu72 according to an embodiment of the present invention can be used for the prevention and treatment of liver cancer because it exhibits the effect of preventing and treating liver fibrosis.

Example 9: Induction of HCC According to Applying STAM Model (Streptozotocin-High Fat Diet Model), Analysis of HCC Markers and Inhibitory Effect of Ssu72 on HCC Mice to which the STAM model is applied are accompanied by steatosis and NASH phenotype, and as HFD feeding period increases, severe HCC may appear. However, due to the limitations of the STAM model, upon long-term observation, some mice die, thus the present inventors first established the minimum period for expressing the HCC phenotype in order to establish a liver cancer model. Normal mice to which the STAM model was applied were sacrificed at 12 weeks of age and excised livers were analyzed. The corresponding experiment schedule is schematically illustrated in FIG. 9A. At 12 weeks after application of the STAM model, liver tissue obtained from sacrificed mice was fixed and analyzed by H&E staining. As a result, tumor lesions were identified and, distribution and shape of cells different from normal tissues were observed. IHC analysis was performed using the CD10 and CD34 antibodies, which are known as HCC markers, at the lesions. Although CD10 is a cell surface protein expressed in various cells, its expression is increased in several cancer types, especially in HCC, so it is used as a marker to distinguish HCC from metastatic cancer that has metastasized to the liver (W G McCluggage et al., *Histopathol.* 39:273-278, 2001). CD34 is expressed in endothelial cells of sinusoid-like vessels of HCC and is an indicator of HCC (MacSween's Pathology of the liver, 2017 May; 22). It was observed that the expression of the two markers was significantly increased compared to the control group, a normal diet mouse (FIG. 9B). Therefore, the above results suggest that HCC develops at 12 weeks after applying the STAM model.

Based on the identified HCC onset, the present inventors administered AAV8 Ssu72 and control AAV8 at week 12, which is the time point of the STAM model containing HCC ($3 \times 10^{10}$ gc/g), and verified the therapeutic effect on HCC 4 weeks later. The corresponding experiment schedule is schematically illustrated in FIG. 9C. The liver of the control group administered with AAV8 was not smooth on the surface and nodules were visually observed, whereas the shape of the liver of the group administered with AAV8 Ssu72 was similar to that of a normal liver (FIG. 9D). The tissue was fixed and HCC markers CD10, CD34, VEGF, and PCNA were analyzed using IHC. VEGF is a growth factor that promotes the formation of blood vessels, and is used as a cancer marker because it is overexpressed in cancer and induces angiogenesis. PCNA is a protein whose expression increases in the nucleus when cells proliferate. Since liver cells rarely divide under normal conditions and cancer cells show uncontrolled cell proliferation, PCNA expression can be observed in actively dividing cancer cells. Expression of the four markers was hardly seen in the AAV8 Ssu72-administered group compared to the control group, and it was confirmed that the shape and distribution of cells in the tissues were similar to those of normal tissues. The quantifying the colorimetric intensity in the IHC experiment using the Image J program are summarized in FIG. 9D. Therefore, the above results suggest that AAV8 Ssu72 can be used as a method for treating liver cancer because it exhibits a therapeutic effect on liver cancer.

In conclusion, the pharmaceutical composition for preventing or treating liver cancer comprising the Ssu72 protein or a nucleotide encoding the Ssu72 protein according to an embodiment of the present invention inhibits the severity and progression of non-alcoholic steatohepatitis (NASH) without side effects, thereby preventing and treating liver fibrosis. Thus, it can be used as a therapeutic agent for the treatment of various types of liver cancer.

Although the present invention has been described with reference to the above-described examples, these are merely exemplary, and those skilled in the art will understand that various modifications and equivalent other embodiments are possible therefrom. Therefore, the true scope of the present invention should be determined by the technical features of the appended claims.

INDUSTRIAL APPLICABILITY

The present invention is drawn to a pharmaceutical composition for treating liver cancer. Thus, the present invention can be used for manufacturing therapeutic agents, especially therapeutic agents for treating liver cancer such as hepatocellular carcinoma.

The present invention was developed during the research on the deduction of drug candidate substances for gene therapy for treating nonalcoholic steatohepatitis in the national new drug development project (Project ID No.: 1465034859, Project No.: HN21C0805000021, Project period: 2021.09.01-2023.08.31), which is a research project supported by multiple ministries of Korean government and the Korea Health Industry Promotion Agency, and executed by one of the present applicant, CUROGEN Technology, Co. Ltd.

The invention claimed is:

1. A method for treating a patient suffering from liver cancer comprising administering to the patient an adeno-associated virus (AAV) vector comprising a polynucleotide encoding a Ssu72 peptide and a liver-specific promoter operably linked to the polynucleotide, and wherein the AAV vector is administered by a systemic administration or an intrahepatic administration.

2. The method according to claim 1, wherein the Ssu72 peptide has the amino acid sequence of SEQ ID NO: 1.

3. The method according to claim 2, wherein the Ssu72 peptide is encoded by a polynucleotide having the nucleotide sequence of SEQ ID NO: 2.

4. The method according to claim 1, wherein the AAV vector is an AAV8 vector.

5. The method according to claim 1, the liver-specific promoter is a thyroxin-binding globulin (TBG) promoter, a PBGD promoter, an α-1 anti-trypsin promoter (EhAlbAAT), a Hepatic Control Region (HCR)-ApoCII hybrid promoter, an HCR-hAAT hybrid promoter, an apolipoprotein E (ApoE) promoter, a phosphoglycerate kinase (PGK) promoter, or a hybrid liver-specific promoter (HLP).

6. The method according to claim 5, wherein the TBG promoter comprises SEQ ID NO: 3.

* * * * *